(12) United States Patent
Bold et al.

(10) Patent No.: US 8,034,814 B2
(45) Date of Patent: Oct. 11, 2011

(54) PHTHALAZINE DERIVATIVES WITH ANGIOGENESIS INHIBITING ACTIVITY

(75) Inventors: Guido Bold, Gipf-Oberfrick (CH); Paul William Manley, Arlesheim (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/953,837

(22) Filed: Nov. 24, 2010

(65) Prior Publication Data

US 2011/0130399 A1    Jun. 2, 2011

Related U.S. Application Data

(60) Continuation of application No. 12/141,179, filed on Jun. 18, 2008, now abandoned, which is a division of application No. 10/475,419, filed as application No. PCT/EP02/04892 on May 3, 2002, now Pat. No. 7,399,761.

(30) Foreign Application Priority Data

May 4, 2001 (GB) .................................. 0111078.2

(51) Int. Cl.
C07D 401/06 (2006.01)
A61K 31/502 (2006.01)
(52) U.S. Cl. .................... 514/252.03; 544/116; 544/238
(58) Field of Classification Search .................. 544/116, 544/238; 514/252.03
See application file for complete search history.

(56) References Cited

U.S. PATENT DOCUMENTS

| 3,753,988 A | 8/1973 | Rodway et al. |
| 4,665,181 A | 5/1987 | Thomas et al. |

FOREIGN PATENT DOCUMENTS

| EP | 0 600 831 A1 | 6/1994 |
| EP | 0 722 936 | 7/1996 |
| GB | 871753 | 5/1958 |
| JP | A03106875 | 5/1991 |
| WO | 97/26258 | 7/1997 |
| WO | 98/35958 | 8/1998 |
| WO | 00/59509 | 10/2000 |
| WO | 01/10859 | 2/2001 |

OTHER PUBLICATIONS

Crespi, Charles et al., "Fluorometric screening for metabolism-based drug-drug interactions," Journal of Pharmacological and Toxicological Methods, vol. 44, pp. 325-331 (2000).
Hennequin, Laurent et al., "Design and structure-Activity relationship of a new class of potent VEGF receptor tyrosine kinase inhibitors," J. Med. Chem., vol. 42, pp. 5369-5389 (1999).
Penolazzi, Letizia et al., "Direct transfection of polymerase chain reaction-generated DNA fragments into mammalian cells employing ethidium bromide indicator and ultrafiltration," Analytical Biochemistry, vol. 248, pp. 190-193 (1997).
Crespi, Charles et al., "Microtiter plate assays for inhibition of human, drug-metabolizing cytochromes P450," Analytical Biochemistry, vol. 248, pp. 188-190 (1997).

*Primary Examiner* — Kahsay T Habte

(57) ABSTRACT

The invention relates to new phthalazine derivatives of formula I,

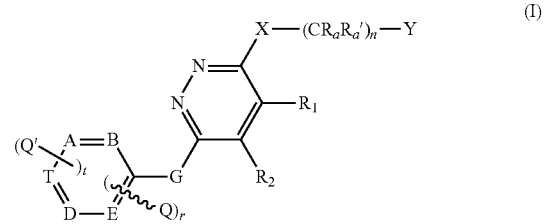

and to processes for the preparation thereof, the application thereof in a process for the treatment of the human or animal body, the use thereof alone or in combination with one or more other pharmaceutically active compounds for the treatment especially of a disease that responds to the inhibition of especially the vascular endothelial growth factor receptor kinase, preferably the treatment of a proliferative disease, or the treatment of inflammatory rheumatic or rheumatoid arthritis and/or pain; and the use of such a compound alone or in combination with one or more other pharmaceutically active compounds for the manufacture of a pharmaceutical preparation for the treatment of said diseases in an animal.

6 Claims, No Drawings

PHTHALAZINE DERIVATIVES WITH ANGIOGENESIS INHIBITING ACTIVITY

The invention relates to new phthalazine derivatives, processes for the preparation thereof, the application thereof in a process for the treatment of the human or animal body, the use thereof alone or in combination with one or more other pharmaceutically active compounds for the treatment of a disease, especially of a disease that responds to the inhibition of tyrosine kinases, more especially the inhibition of the vascular endothelial growth factor (VEGF) receptor kinase, preferably the treatment of a proliferative disease, such as a tumour disease or a disease caused by ocular neovascularisation, such as age-related macula degeneration or diabetic retinopathy, or the treatment of inflammatory rheumatic or rheumatoid arthritis and/or pain; a method for the treatment of such disease in an animal, especially in a human, and the use of such a compound alone or in combination with one or more other pharmaceutically active compounds for the manufacture of a pharmaceutical preparation for the treatment of said diseases in an animal, especially in humans.

The angiogenic factor known as "Vascular Endothelial Growth Factor" (VGEF), along with its cellular receptors, lies at the centre of the network regulating the growth and differentiation of the vascular system and its components, both during embryonic development and normal growth and in a wide number of pathological anomalies and diseases (see Breier, G., et al., Trends in Cell Biology 6, 454-6 [1996] and references cited therein). A number of isoforms of VEGF are known which show comparable biological activity, but differ in the type cells that secrete them and in their heparin-binding capacity. The receptors for VEGF are transmembranous receptor tyrosine kinases and have an extracellular domain and an intracellular tyrosine kinase domain. Various types are known, e.g. VEGFR-1, VEGFR-2, and VEGFR-3.

Angiogenesis is regarded as an absolute prerequisite for those tumours which grow beyond a maximum diameter of about 1-2 mm; up to this limit, oxygen and nutrients may be supplied to the tumour cells by diffusion. Every tumour, regardless of its origin and its cause, is thus dependent on angiogenesis for its growth after it has reached a certain size. A number of publications and patent applications, e.g. WO 98/35958, WO 00/59509 and WO 01/10859, disclose certain phthalazine derivatives that are capable of VEGF receptor inhibition.

One class of metabolising enzymes that are especially important in the metabolism of xenobiotics, biotics, such as drugs, is represented by the Cytochrome P 450-dependent family of isoenzymes (CyP 450 hereinafter). CyP 450-dependent monoxygenases are a supergene family of enzymes that catalyse the oxidation of mainly lipophilic chemicals through the insertion of one atom from molecular oxygen into the substrate, resulting, for example, in aliphatic and aromatic hydroxylations and epoxidations of olefinic or aromatic double bonds, respectively. They can usually be found in the microsomal fraction of cell lysates. More than 20 isoenzymes of CyP 450-depending monoxygenases are known in human, partially with overlapping, but often defined substrate specificities. In view of their amino acid sequences and their resulting substrate specificity and specific inducibility, the different isoenzymes are classified into different families. For the metabolism of xenobiotics, the families 1 to 4 are especially important, each of which is again subclassified into subfamilies (A, B, . . . ). Examples are CyP1A, CyP2C, CyP2D or CyP3A. Each of these subclasses is further split into sub-subclasses, e.g. Cyp2C8, Cyp2C9 or CyP3A4, and polymorphism may be present.

The group of CyP 450-dependent enzymes has both harmful and beneficial activities. Metabolic conversion of xenobiotics to toxic, mutagenic and carcinogenic forms is a harmful activity. Detoxification of some drugs or the activation of drugs to their active form are examples of beneficial activities.

Especially in the field of tumor treatment, but also in other areas, two or more drugs are combined, for example in order to take advantage of synergistic effects or in the parallel treatment of two diseases at the same time. A possible disadvantage in such combination that the compounds may interfere with each other by mutual inhibition of metabolising enzymes, such as the Cyp 450 monoxygenases. This can lead to drastical changes in pharmacokinetics, leading to elevated levels of drugs the metabolism of which is inhibited by co-administered drugs, and may thus lead to adverse drug reactions, e.g. due to elevated toxicity of the unmetabolized drugs, or to inefficiency if only the metabolised drug is pharmaceutically active, etc. Also when used alone, drugs may influence normal physiological processes by inhibiting normal biosynthetic or metabolic enzymes, thus interfering with biochemical processes in the living being. It is therefore desirable to design drugs that show no or low inhibition of CyP 450 hemoproteins.

With this background, it is the problem of the present invention to provide a novel advantageous class of phthalazine derivatives that especially display a low level of inhibition on enzymes that metabolise xenobiotics, especially drugs, preferably low inhibition of Cyp 450-dependent enzymes, thus inter alia allowing for predictably low interactions with other xenobiotics or substrates present in the body, better pharmacokinetic and pharmacodynamic behaviour, and/or display superior tyrosine kinase inhibiting properties, especially regarding the inhibition of VEGF receptor tyrosine kinase.

Surprisingly, it has now been found that phthalazine derivatives of formula I, described hereinafter, have advantageous pharmacological properties and show advantageous VEGF receptor tyrosine kinase inhibiting activity, allowing inter alia treatment of VEGF-dependent cell proliferation, the treatment of especially inflammatory rheumatic or rheumatoid diseases, such as rheumatoid arthritis, and/or of pain, or the other diseases mentioned above and below, especially at the same time showing lower levels of inhibition on enzymes that metabolise xenobiotics, especially of CyP 450-dependent enzymes, leading to more predictable pharmacokinetic and pharmacodynamic behaviour, especially in combination with xenobiotics present in food or drugs.

The compounds of formula I permit thus a better therapeutic approach, especially for diseases in the treatment of which, and also for the prevention of which, an inhibition of angiogenesis and/or of the VEGF receptor tyrosine kinase shows beneficial effects.

The invention relates to a compound of the formula I,
A compound of the formula I,

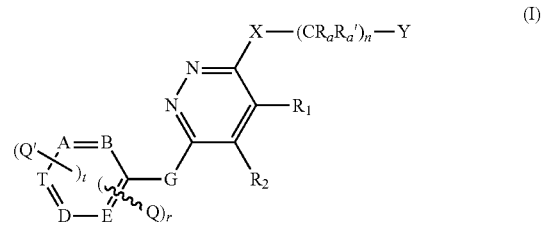

wherein
r is 1 or 2,
n is 0 to 3,
t is 0, 1 or 2,
$R_1$ and $R_2$
a) are independently in each case a lower alkyl;
b) together form a bridge of subformula I*,

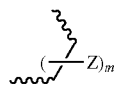

(I*)

wherein the bond is achieved via the two terminal C atoms and
m is 0 to 4, or
c) together form a bridge of subformula I**,

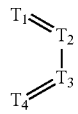

(I**)

wherein one or two of the ring members $T_1$, $T_2$, $T_3$ and $T_4$ are nitrogen, and the others are in each case CH, and the bond is achieved via atoms $T_1$ and $T_4$;

G is —C(=O)—, —CHF—, —CF$_2$—, lower alkylene, $C_2$-$C_6$alkenylene, lower alkylene or $C_3$-$C_6$alkenylene substituted by acyloxy or hydroxy, —CH$_2$—O—, —CH$_2$—S—, —CH$_2$—NH—, —CH$_2$—O—CH$_2$—, —CH$_2$—S—CH$_2$—, —CH$_2$—NH—CH$_2$—, oxa (—O—), thia (—S—), imino (—NH—), —CH$_2$—O—CH$_2$—, —CH$_2$—S—CH$_2$—, —CH$_2$—NH—CH$_2$—, —(C(R$_4$)$_2$)$_t$—S(O)$_p$-(5-membered heteroaryl)-(C(R$_4$)$_2$)$_s$—, —(C(R$_4$)$_2$)$_t$—C(G$_1$)(R$_4$)—(C(R$_4$)$_2$)$_s$—, —O—CH$_2$—, —S(O)—, —S(O$_2$)—, —SCH$_2$—, —S(O)CH$_2$—, —CH$_2$S(O)— or —CH$_2$S(O)$_2$—, wherein each of p, s and t, independently of the other, is 0, 1 or 2; $R_4$ is hydrogen, halogen or lower alkyl; and $G_1$ is —CN, —CO$_2$R$_3$, —CON(R$_6$)$_2$ or CH$_2$N(R$_6$)$_2$, wherein $R_3$ is hydrogen or lower alkyl and $R_6$ is hydrogen, alkyl, aryl or aryl-lower alkyl;

A, B, D, E and T are independently N or CH subject to the proviso that at least one and not more than three of these radicals are N;

Q is either lower alkoxy or O (oxo), with the proviso that if Q is lower alkoxy, the waved line representing the bonding of Q is a single bond and the ring carrying Q has three double bonds, and if Q is O, the waved line representing the bonding of Q is a double bond and for each Q=O, one of the double bonds in the ring is changed to a single bond; and with the proviso that any Q is bonded to a ring C atom;

Q' is halogen, NHR$^Q$, NR$^Q_2$, OR$^Q$, SR$^Q$, alkyl, aryl-alkyl, cyclohexyl-alkyl, perfluoroalkyl, acyl, substituted or unsubstituted aryl, or substituted or unsubstituted hetaryl, wherein R$^Q$ represents acyl, alkyl, or alkyl substituted by hydroxy or halogen;

$R_a$ and $R_a'$ are each independently H, halogen or lower alkyl;
X is imino, oxa, or thia;
Y is hydrogen, substituted or unsubstituted aryl, substituted or unsubstituted heteroaryl, or unsubstituted or substituted cycloalkyl; and Z is mono- or disubstituted amino, halogen, alkyl, cycloalkyl, substituted alkyl, hydroxy, etherified or esterified hydroxy, nitro, cyano, carboxy, esterified carboxy, —OCOR$_6$, —CH$_2$OR$_3$, —OCO$_2$R$_3$, alkanoyl, carbamoyl, N-mono- or N,N-disubstituted carbamoyl, amidino, guanidine, mercapto, sulfo, alkylthio, especially lower alkylthio, halogenated lower alkylthio, arylthio, especially phenylthio or alkylphenylthio, aryl lower alkylthio, especially phenyl lower alkylthio, arylsulfinyl, especially phenylsulfinyl or alkylphenylsulfinyl, aryl-lower alkylsulfinyl, especially phenyl-lower alkylsulfinyl, alkylsulfonyl, especially lower alkylsulfonyl, halogeno-lower alkylsulfonyl, arylsulfonyl, especially phenylsulfonyl or alkylphenylsulfonyl, aryl-lower alkylsulfonyl, especially phenyl-lower alkylsulfonyl, ureido, $C_2$-$C_7$alkenyl, aryl, heteroaryl, especially pyrazolyl or lower-alkyl pyrazolyl, optionally substituted saturated heterocyclyl, heteroarylalkyl, heteroaryloxy, —S(O)$_p$(heteroaryl) or —S(O)$_p$(heteroarylalkyl) wherein p is 0, 1 or 2, heteroaryloxy, —CHO or —OCON(R$_6$)$_2$, —NR$_3$CO$_2$R$_6$ or
—NR$_3$CON(R$_6$)$_2$ wherein $R_3$ and $R_6$ are as defined above; wherein—if more than 1 radical Z (m≧2) is present—the substituents Z are selected independently from each other, and wherein $R_3$ and $R_6$ are as defined above;

and wherein the bonds characterized in subformula I* by a wavy line are either single or double bonds;

with the proviso that when two groups $R_6$ are each alkyl and located on the same nitrogen atom, they may be linked by a bond, an O, an S or NR$_3$ with $R_3$ as defined above to form a N-containing heterocycle of 5 to 7 ring atoms;

and with the proviso that only compounds other than those wherein r is 1, n is 0, $R_1$ and $R_2$ together form a bridge of subformula I* wherein m is 0 and the waved lines represent double bonds, respectively, G is —CH$_2$—, T is N, each of A, B, E and T is CH, Q is methoxy and Y is 4-methyl-3-bromo-phenyl, 4-ethyl-3-bromo-phenyl, 3-chloro-5-trifluoromethyl-phenyl or 4-isopropyl-3-methyl-phenyl fall under the claim;

or an N-oxide of a compound of formula I, wherein 1 or more N atoms carry an oxygen atom;
or a tautomer or mixture of tautomers of a compound of formula I or an N-oxide thereof;
or a pharmaceutically acceptable salt of a compound of formula I, of an N-oxide or of a tautomer or mixture of tautomers thereof.

The general terms used hereinbefore and hereinafter preferably have within the context of this disclosure the following meanings, unless otherwise indicated:

The prefix "lower" denotes a radical having up to and including a maximum of 7, especially up to and including a maximum of 4 carbon atoms, the radicals in question being either linear or branched with single or multiple branching.

Where the plural form is used for compounds, salts, and the like, this is taken to mean also a single compound, salt, or the like.

Any asymmetric carbon atoms (for example in compounds of formula I [or an N-oxide thereof], wherein n=1 and R is lower alkyl) may be present in the (R)-, (S)- or (R,S)-configuration, preferably in the (R)- or (S)-configuration. Substituents at a double bond or a ring may be present in cis-(=Z—) or trans (=E-) form. The compounds may thus be present as mixtures of isomers or as pure isomers, preferably as enantiomer-pure diastereomers.

The present invention relates also to possible tautomers of the compounds of formula I. Especially an oxo substituent Q may display tautomerism of the following kind: Thus, a ring of the partial formula IA (forming a part of the formula I),

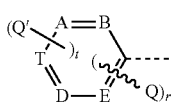
(IA)

wherein each of A, B, D and E is CH, T is N, Q is oxo in 2-position relatively to the N, r is one, and Q' and t are as defined for a compound of formula I above, may show the following tautomerism:

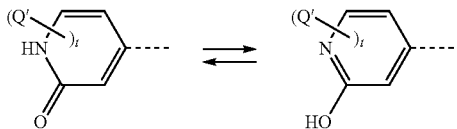

with the form shown on the left (lactam form) prevailing under normal conditions.

In analogy, a ring of the partial formula IA wherein each of A, B, E and T is CH, D is N, Q is oxo in 6-position relatively to the N and r is one, may show the following tautomerism:

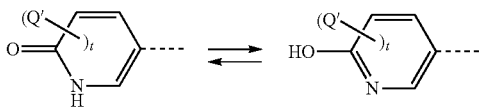

with the form shown on the left (lactam form) prevailing under normal conditions.

Thus, depending on the equilibrium constants and the conditions, a compound of the formula I may be present in the form of a pure tautomer or a mixture of tautomers.

The index r in formula I is preferably 1. Q is preferably oxo.

t is preferably 0 or 1. Q' is preferably halogen or NHR$^Q$, wherein R$^Q$ represents lower alkyl; thiazolyl or furyl. Q' is most preferably bound to a carbon atom and located in α-position to the radical Q.

The index n in formula I is preferably 0 or 1, or it is 2 or 3.

In the preferred embodiment, $R_1$ and $R_2$ together form a bridge of subformula I*. The index m is preferably 0, 1, or 2. In particular, m is preferably 0 or 1, most preferably 0.

In subformula I**, the ring member $T_2$ or $T_3$ is preferably nitrogen, and each of the other ring members are CH.

Of ring members A, B, D, E and T in formula I, not more than 3 may be N, and the remainder are CH. Preferably, A, D or T is N, while the remaining of the ring members A, B, D, E and T are CH, respectively. Most preferably, each of B, D, E and T is CH, while A is N.

In the representation of bivalent groups G, the bond shown on the left side in each case is bound to the ring with ring members A, B, D, and E, whereas the bond shown on the right is bound to the phthalazine ring in formula I.

Lower alkylene, $C_2$-$C_6$alkylene and $C_2$-$C_6$alkenylene G may be branched or, preferably, unbranched and are in particular methylene (where lower alkylene is encompassed) or $C_2$-$C_4$alkylene or $C_2$-$C_4$alkenylene, above all ethylene (—$CH_2$—$CH_2$—), ethenylene, (—CH=CH—), propenylene (—CH=CH—$CH_2$—), propylene (—$CH_2$—$CH_2$—$CH_2$—) or tetramethylene (—$CH_2$—$CH_2$—$CH_2$—$CH_2$—). G is preferably in particular methylene or in a broader aspect of the invention ethylene, ethenylene or propylene. In $C_2$-$C_6$alkenylene G, the substituents on the double bond are preferably present in the E- (=trans-) form.

Acyl is preferably arylcarbonyl, wherein aryl is as defined below, in particular benzoyl, or lower alkanoyl, especially acetyl.

Lower alkylene substituted by hydroxy is especially hydroxymethylene; $C_2$-$C_6$alkylene substituted by hydroxy is preferably hydroxyethylene (—$CH_2$—CH(OH)).

Lower alkyl is especially $C_1$-$C_4$alkyl, e.g. n-butyl, sec-butyl, tert-butyl, n-propyl, isopropyl, or especially methyl or also ethyl.

Aryl is preferably an aromatic radical having 6 to 14 carbon atoms, especially phenyl, naphthyl, fluorenyl or phenanthrenyl, the radicals defined above being unsubstituted or substituted by one or more, preferably up to three, especially one or two substituents, especially selected from the group consisting of amino, mono- or disubstituted amino, halogen, alkyl, alkenyl, such as ethenyl, cycloalkyl, cycloalkenyl, substituted alkyl, hydroxy, etherified or esterified hydroxy, nitro, cyano, carboxy, esterified carboxy, alkanoyl, carbamoyl, N-mono- or N,N-disubstituted carbamoyl, especially N-methylcarbamoyl or N-tert-butylcarbamoyl; amidino, guanidino, mercapto, lower alkylthio, such as methylthio, sulfo, phenylthio, phenyl-lower alkylthio, alkylphenylthio, alkylsulfinyl, phenylsulfinyl, phenyl-lower alkylsulfinyl, alkylphenylsulfinyl, phenylsulfonyl, phenyl-lower alkylsulfonyl, phenyl, lower alkanoyl, such as acetyl, lower alkylmercapto, such as methylmercapto (—S—$CH_3$), halogen-lower alkylthio, such as trifluoromethylthio (—S—$CF_3$), lower alkylsulfonyl, halogen-lower alkylsulfonyl, such as especially trifluoromethane sulfonyl, dihydroxybora (—B(OH)$_2$), heterocyclyl, heterocyclyl lower alkyl, heteroaryloxy, heteroaryl-lower alkoxy, —S(O)$_p$(heteroaryl), —S(O)$_p$(heteroarylalkyl), —CHO, —$CH_2OR_3$, —O—CON($R_6$)$_2$, —$NR_3CO_2R_6$ or —$NR_3$CON($R_6$)$_2$, or where $R_6$ is H, alkyl, aryl (except substituted by aryl or aryl-lower alkyl) or aryl-lower alkyl (with aryl except if substituted by aryl or aryl-lower alkyl), $R_3$ is H or lower alkyl and p is 0, 1 or 2; lower alkylene dioxy bound at adjacent C-atoms of the ring, such as methylene dioxy, ureido and sulfamoyl; for example, aryl is phenyl, which is either unsubstituted or substituted by one or two substituents selected independently of one another from the group consisting of amino; lower alkanoylamino, especially acetylamino; halogen, especially fluorine, chlorine, bromine, or iodine; lower alkyl, especially methyl or preferably ethyl, further propyl or t-butyl; halogen-lower alkyl, especially trifluoromethyl; hydroxy; lower alkoxy, especially methoxy or also ethoxy; phenyl-lower alkoxy, especially benzyloxy; and cyano, or (as an alternative or in addition to the previous group of substituents) $C_8$-$C_{12}$alkoxy, especially n-decyloxy, carbamoyl, lower alkylcarbamoyl, such as n-methyl- or n-tert-butylcarbamoyl, lower alkanoyl, such as acetyl, phenyloxy, halogen-lower alkyloxy, such as trifluoromethoxy or 1,1,2,2-tetrafluoroethyloxy, lower alkoxycarbonyl, such as methoxy-, tert-butoxy- or ethoxycarbonyl, lower alkylmercapto, such as methylmercapto, halogen-lower alkylmercapto, such as trifluoromethylmercapto, hydroxy-lower alkyl, such as hydroxymethyl or 1-hydroxymethyl, lower alkylsulfonyl, such as methane sulfonyl, halogen-lower alkylsulfonyl, such as trifluoromethane sulfonyl, phenylsulfonyl, dihydroxybora (—B(OH)$_2$), 2-methylpyrimidin-4-yl, oxazol-5-yl, 2-methyl-1,3-dioxolan-2-yl, 1H-pyrazol-3-yl, 1-methyl-pyrazol-3-yl and lower alkylenedioxy bound to two adjacent C-atoms, such as methylene dioxy or, alternatively or in addition to the previous group of substituents, ureido, vinyl, pyrazol-3-yl and 1-methyl-pyrazol-3-yl, especially preferred are (especially with regard to a novel compound of the formula I as described hereinbefore and hereinafter) one or two substituents independently selected from lower alkyl, especially methyl, halogen, especially chlorine or bromine, and halogen lower alkyl, especially trifluoromethyl. In the cases where Y is aryl, it is in particular preferred that aryl is phenyl preferably substituted by one or two substituents independently selected from the group consisting of lower alkyl, in particular methyl, ethyl, n-propyl, i-propyl or t-butyl; halogen, in particular fluorine, chlorine, bromine or iodine; lower alkoxy, in particular ethoxy; and halogen lower alkyl, in particular trifluoromethyl; special preference being for substitution by one or two substitutents independently selected from the group consisting of lower alkyl, in particular methyl or t-butyl; halogen, in particular chlorine; and halogen lower alkyl, in particular trifluoromethyl; or that (especially in a novel compound of the formula I) aryl is napthyl, especially 2-naphthyl.

Heteroaryl is preferably a heterocyclic radical unsaturated in the bonding ring and is preferably monocyclic or in a broader sense bicyclic or tricyclic; wherein at least in the ring bonding to the radical of the molecule of formula I one or more, preferably one to four, especially one or two carbon atoms of a corresponding aryl radical are substituted by a heteroatom selected from the group consisting of nitrogen, oxygen and sulfur, the bonding ring preferably having 4 to 12, especially 5 to 7 ring atoms; or is a saturated analogue of such an unsaturated heteroaryl; heteroaryl being unsubstituted or substituted by one or more, especially 1 to 3, independently selected from the group consisting of the substituents defined above as substituents of aryl; and especially being a heteroaryl radical selected from the group consisting of imidazolyl, thienyl, furyl, pyranyl, thianthrenyl, isobenzofuranyl, benzofuranyl, chromenyl, 2H-pyrrolyl, pyrrolyl, lower alkyl-substituted imidazolyl, benzimidazolyl, pyrazolyl, thiazolyl, isothiazolyl, oxazolyl, isoxazolyl, pyridyl, pyrazinyl, pyrimidinyl, pyridazinyl, indolizinyl, isoindolyl, 3H-indolyl, indolyl, indazolyl, triazolyl, tetrazolyl, purinyl, 4H-quinolizinyl, isoquinolyl, quinolyl, phthalazinyl, naphthyridinyl, quinoxalyl, quinazolinyl, cinnolinyl, pteridinyl, carbazolyl, phenanthridinyl, acridinyl, perimidinyl, phenanthrolinyl and furazanyl, or a saturated analogue thereof, especially dioxanyl, preferably [1,3]dioxan-5-yl; each of these radicals being bonded to at least one heteroatom and the radical of the molecule of formula I via a ring and each of these radicals being unsubstituted or substituted by one to two radicals selected from the group consisting of lower alkyl, especially methyl, propyl, isopropyl or tert-butyl, lower alkoxy, especially methoxy, and halo, especially bromo or chloro; pyridyl is especially preferred; also especially preferred are quinolyl, especially quinolin-6-yl; lower alkyl-pyridyl, especially 5-methyl-pyridin-2-yl or 6-methyl-pyridin-2-yl; lower alkylpyrimidinyl, especially 4-methylpyrimidin-2-yl or 6-tert-butyl-pyrimidin-4-yl; halo-lower alkylpyridyl, especially 5-trifluoromethyl-pyridin-2-yl; lower alkoxy-pyridyl, especially 5-methoxy-pyridin-2-yl; di-lower alkyl-pyridyl, especially 2,6-dimethyl-pyridin-4-yl or 4,6-dimethyl-pyridin-2-yl; di-lower alkylpyrimidinyl, especially 2,6-dimethyl-pyrimidin-4-yl; or halo-pyridyl, especially 5-bromo-pyridin-2-yl or 6-chloro-pyridin-3-yl; or lower-alkyl-[1,3]dioxan-5-yl, such as cis, trans-, cis- or preferably trans-2-isopropyl-[1,3]dioxan-5-yl. Pyridyl Y is preferably 3- or 4-pyridyl.

Mono- or disubstituted amino is especially amino substituted by one or two radicals selected independently of one another from alkyl, especially lower alkyl, such as methyl; hydroxy-lower alkyl, such as 2-hydroxyethyl; halogen-lower alkyl; amino-lower alkyl; N-lower alkylamino-alkyl; N,N-di-lower alkylamino-alkyl, phenyl-lower alkyl; N-lower alkanoylamino-alkyl; N,N-di-lower alkanoylamino-alkyl; cyanoalkyl; carboxyalkyl; lower-alkoxycarbonylalkyl; phenyl-lower alkoxycarbonylalkyl; lower alkanoyl, such as acetyl; benzoyl; substituted benzoyl, wherein the phenyl radical is unsubstituted or especially substituted by one or more, preferably one or two, substituents selected from nitro or amino, or also from halogen, amino, N-lower alkyl-amino, N,N-di-lower alkylamino, hydroxy, cyano, carboxy, lower alkoxycarbonyl, lower alkanoyl, and carbamoyl; and phenyl-lower alkoxycarbonyl, wherein the phenyl radical is unsubstituted or especially substituted by one or more, preferably one or two, substituents selected from nitro or amino, or also from halogen, amino, N-lower alkylamino, N,N-di-lower alkylamino, hydroxy, cyano, carboxy, lower alkoxycarbonyl, lower alkanoyl, and carbamoyl; and is preferably N-lower alkylamino, such as N-methylamino, hydroxy-lower alkylamino, such as 2-hydroxyethylamino, phenyl-lower alkylamino, such as benzylamino, N,N-di-lower alkylamino, N-phenyl-lower alkyl-N-lower alkylamino, N,N-di-lower alkylphenylamino, lower alkanoylamino, such as acetylamino, or a substituent selected from the group consisting of benzoylamino and phenyl-lower alkoxycarbonylamino, wherein the phenyl radical in each case is unsubstituted or especially substituted by nitro or amino, or also by halogen, amino, N-lower alkylamino, N,N-di-lower alkylamino, hydroxy, cyano, carboxy, lower alkoxycarbonyl, lower alkanoyl or carbamoyl, or as an alternative or in addition to the previous group of radicals by aminocarbonylamino.

Halo or halogen is above all fluorine, chlorine, bromine, or iodine, especially fluorine, chlorine, or bromine.

Alkyl (alone or as part of radicals, e.g. halogenalkyl or the like) has preferably up to a maximum of 12 carbon atoms and is especially lower alkyl, especially methyl, or also ethyl, n-propyl, isopropyl, or tert-butyl.

Substituted alkyl is alkyl as last defined, especially lower alkyl, preferably methyl; where one or more, especially up to three, substituents may be present, primarily from the group selected from halogen, especially fluorine, and also from amino, N-lower alkylamino, N,N-di-lower alkylamino, N-lower alkanoylamino, hydroxy, cyano, carboxy, lower alkoxycarbonyl, and phenyl-lower alkoxycarbonyl. Trifluoromethyl is especially preferred. In a novel compound of the formula I, methyl is especially preferred.

Aryl-lower alkyl is lower alkyl that is substituted (preferably terminally) by aryl as defined above.

Heteroaryl-lower alkyl is lower alkyl that is substituted (preferably terminally) by heteroaryl as defined above.

Optionally substituted saturated heterocyclyl is preferably a saturated analogue of heteroaryl as described above which is unsubstituted or substituted as described for heteroaryl.

When two groups $R_6$ are each alkyl and located on the same nitrogen atom, and they are linked by a bond, an O, an S or $NR_3$ with $R_3$ as defined above to form a N-containing heterocycle of 5 to 7 ring atoms, preferred examples of such heterocycles, including the N to which they are attached, are:

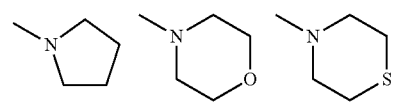

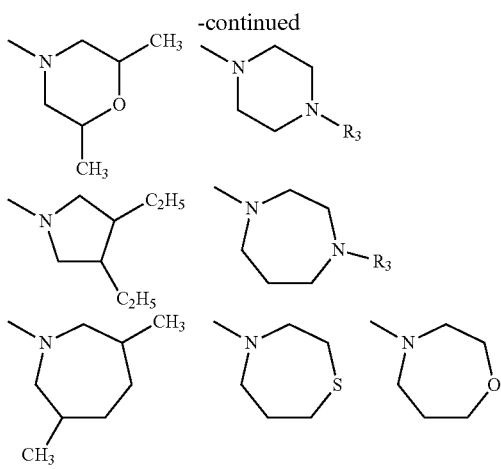

Etherified hydroxy is especially $C_8$-$C_{20}$alkyloxy, such as n-decyloxy, lower alkoxy (preferred), such as methoxy, ethoxy, isopropyloxy, or n-pentyloxy, phenyl-lower alkoxy, such as benzyloxy, or also phenyloxy, or as an alternative or in addition to the previous group halogen-lower alkyloxy, such as trifluoromethyloxy or 1,1,2,2-tetrafluoroethoxy.

Esterified hydroxy is especially lower alkanoyloxy, benzoyloxy, lower alkoxycarbonyloxy, such as tert-butoxycarbonyloxy, or phenyl-lower alkoxycarbonyloxy, such as benzyloxycarbonyloxy.

Esterified carboxy is especially lower alkoxycarbonyl, such as tert-butoxycarbonyl or ethoxy-carbonyl, or further methoxycarbonyl, phenyl-lower alkoxycarbonyl, or phenyloxycarbonyl.

Alkanoyl is above all alkylcarbonyl, especially lower alkanoyl, e.g. acetyl.

N-mono- or N,N-disubstituted carbamoyl is especially substituted by one or two substituents selected from the group consisting of lower alkyl, especially methyl, phenyl-lower alkyl, or hydroxy-lower alkyl, at the terminal nitrogen atom.

Alkylphenylthio is especially lower alkylphenylthio.

Alkylphenylsulfinyl is especially lower alkylphenylsulfinyl.

Halo-lower alkylthio is preferably trifluoromethylthio.

Halo-lower alkansulfonyl is preferably trifluormethylsulfonyl.

Pyrazolyl is preferably pyrazol-3-yl, lower alkylpyrazolyl is preferably 1-methyl-pyrazol-3-yl.

$C_2$-$C_7$-Alkenyl is preferably vinyl.

Unsubstituted or substituted cycloalkyl has 3 to 12 ring carbon atoms, and is preferably $C_3$-$C_8$cycloalkyl, which is unsubstituted or substituted in the same way as aryl, especially as defined for phenyl. Cyclohexyl, in a broader sense cyclopentyl or cyclopropyl, are preferred.

Cycloalkenyl is a non-aromatic unsaturated carbocycle that contains between 3 and 12, preferably 3 to 8, carbon atoms and up to three double bonds, with the proviso that cycloalkenyl groups that differ from aromatics by lacking only one double bond (such as cyclohexadiene) which are not sufficiently non-reactive are not comprised.

Z in a compound of the formula I is preferably amino, hydroxy-lower alkylamino, such as 2-hydroxyethylamino, lower alkanoylamino, such as acetylamino, nitrobenzoylamino, such as 3-nitrobenzoylamino, aminobenzoylamino, such as 4-aminobenzoylamino, phenyl-lower alkoxycarbonylamino, such as benzyloxycarbonylamino, or halogen, such as bromine; preferably only one substituent is present (m=1), especially one of the last mentioned, especially halogen. A compound of formula I wherein $R_1$ and $R_2$ together form a bridge of the subformula I*, especially a compound of the formula IA wherein Z is absent (m=0), is quite especially preferred.

Heterocyclyl is especially a five or six-membered heterocyclic system with 1 or 2 heteroatoms selected from the group consisting of nitrogen, oxygen, and sulfur, which may be unsaturated or wholly or partly saturated, and is unsubstituted or substituted, especially by lower alkyl, such as methyl; a radical selected from 2-methylpyrimidin-4-yl, oxazol-5-yl, 2-methyl-1,3-dioxolan-2-yl, 1H-pyrazol-3-yl, and 1-methyl-pyrazol-3-yl is preferred.

Aryl in the form of phenyl which is substituted by lower alkylene dioxy bound to two adjacent C-atoms, such as methylene dioxy, is preferably 3,4-methylene dioxyphenyl.

If Q is O (oxo), the waved line representing the bonding of Q is a double bond and for each Q=O, one of the double bonds (namely the one that would otherwise start from the ring carbon atom binding Q) in the ring is changed to a single bond; preferably, the moieties A, B, D, E and T are chosen such that any carbon A, B, D, E or T binding Q is directly bound to an N or (if Q is oxo) to an NH.

Where a substituent such as Q or Z is present, an H atom of the binding atom to which these moieties are attached is replaced by such substituent.

The bonds in subformula I* characterized by wavy lines are present either as single or as double bonds. Preferably both at the same time are either single or double bonds. It is especially preferred when both are double bonds at the same time.

The bridges formed from $R_1$ and $R_2$ in formula I and formula IA which are of subformula I* or I** form, together with the carbon atoms bonding $R_1$ and $R_2$, a ring with 6 ring atoms.

An N-oxide of a compound of formula I is preferably an N-oxide in which a phthalazine-ring nitrogen or a nitrogen in the ring with ring members A, B, D, and E carries an oxygen atom, or several of said nitrogen atoms carry an oxygen atom. Preferred are compounds without N-oxide moiety.

Salts are especially the pharmaceutically acceptable salts of compounds of formula I (or an N-oxide or tautomer or mixture of tautomers thereof).

Such salts are formed, for example, as acid addition salts, preferably with organic or inorganic acids, from compounds of formula I (or an N-oxide or tautomer or mixture of tautomers thereof) with a basic nitrogen atom, especially the pharmaceutically acceptable salts. Suitable inorganic acids are, for example, halogen acids, such as hydrochloric acid; sulfuric acid; or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, 2-hydroxybutyric acid, gluconic acid, glucosemono-carboxylic acid, fumaric acid, succinic acid, adipic acid, pimelic acid, suberic acid, azelaic acid, malic acid, tartaric acid, citric acid, glucaric acid, galactaric acid, amino acids, such as glutamic acid, aspartic acid, N-methylglycine, acetylaminoacetic acid, N-acetylasparagine or N-acetylcysteine, pyruvic acid, acetoacetic acid, phosphoserine, 2- or 3-glycerophosphoric acid, maleic acid, hydroxymaleic acid, methylmaleic acid, cyclohexanecarboxylic acid, benzoic acid, salicylic acid, 1- or 3-hydroxynaphthyl-2-carboxylic acid, 3,4,5-trimethoxybenzoic acid, 2-phenoxybenzoic acid, 2-acetoxybenzoic acid, 4-aminosalicylic acid, phthalic acid, phenylacetic acid, glucuronic acid, galacturonic acid, methane- or ethanesulfonic acid, 2-hydroxyethanesulfonic acid, ethane-1,2-disulfonic acid, benzenesulfonic acid, 2-naphthalenesulfonic acid, 1,5-naphthalenedisulfonic acid, N-cyclohexylsulfamic acid, N-methyl-, N-ethyl- or N-propylsulfamic acid, or other organic protonic acids, such as ascorbic acid.

In the presence of negatively charged radicals, such as carboxy or sulfo, salts may also be formed with bases, e.g. metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N,N'-dimethylpiperazine.

In the presence of a basic group and an acid group in the same molecule, a compound of formula I (or an N-oxide or tautomer or mixture of tautomers thereof) may also form internal salts.

For isolation or purification purposes it is also possible to use pharmaceutically unacceptable salts, for example picrates or perchlorates. Only the pharmaceutically acceptable salts or free compounds (if the occasion arises, in the form of pharmaceutical preparations) attain therapeutic use, and these are therefore preferred.

In view of the close relationship between the novel compounds in free form and in the form of their salts, including those salts that can be used as intermediates, for example in the purification or identification of the novel compounds, their tautomers or tautomeric mixtures and their salts and the N-oxides or the salts thereof, any reference hereinbefore and hereinafter to compounds of the formula I is to be understood as referring also to the corresponding N-oxides, tautomers of compounds of the formula I or their N-oxides, tautomeric mixtures of compounds of the formula I or their N-oxides, or salts of any of these, as appropriate and expedient and if not mentioned otherwise.

The compounds of formula I have valuable pharmacological properties, as described hereinbefore and hereinafter.

The efficacy of the compounds of the formula I as inhibitors of VEGF-receptor tyrosine kinase activity can be demonstrated as follows:

Test for activity against VEGF-receptor tyrosine kinase: the test is conducted using Flt-1 VEGF-receptor tyrosine kinase. The detailed procedure is as follows: 30 µl kinase solution (10 ng of the kinase domain of Flt-1, Shibuya et al., Oncogene 5, 519-24 [1990]) in 20 mM Tris.HCl pH 7.6, 3 mM manganese dichloride ($MnCl_2$), 3 mM magnesium chloride ($MgCl_2$) and 3 µg/ml poly(Glu,Tyr) 4:1 (Sigma, Buchs, Switzerland), 8 µM [$^{33}$P]-ATP (0.2 µCi/batch), 1% dimethyl sulfoxide, and 0 to 50 µM of the compound to be tested are incubated together for 15 minutes at room temperature. The reaction is then ended by the addition of 10 µl 0.25 M ethylenediaminetetraacetate (EDTA) pH 7. Using a multichannel dispenser (LAB SYSTEMS, USA), an aliquot of 20 µl is applied to a PVDF (=polyvinyl difluoride) Immobilon P membrane (Millipore, USA), which is incorporated into a Millipore microtiter filter manifold, and connected to a vacuum. Following complete elimination of the liquid, the membrane is washed 4 times successively in a bath containing 0.5% phosphoric acid ($H_3PO_4$), incubated for 10 minutes each time while shaking, then mounted in a Hewlett Packard TopCount Manifold and the radioactivity measured after the addition of 10 µl Microscint® (β-scintillation counter liquid; Packard USA). $IC_{50}$-values are determined by linear regression analysis of the percentages for the inhibition of each compound in three concentrations (as a rule 0.01, 0.1, and 1 µM). Preferably inhibitory concentrations ($IC_{50}$ with 50% maximum inhibition versus control without inhibitory substance of formula I) in the range 10 nmol/liter to 100 µmol/liter are found here, especially in the range 10 to 2000 nmol/liter.

The antitumour efficacy of the compounds of formula I can be demonstrated in vivo as follows:

In vivo activity in the nude mouse xenotransplant model: female BALB/c nude mice (8-12 weeks old, for example Novartis Animal Farm, Sisseln, Switzerland) are kept under sterile conditions with water and feed ad libitum. Tumours are induced by subcutaneous injection of tumour cells (human epithelial cell line A-431; American Type Culture Collection (ATCC), Rockville, Md., USA, Catalogue Number ATCC CRL 1555; cell line from an 85-year-old woman; epidermoid carcinoma cell line) into carrier mice. The resulting tumours pass through at least three consecutive transplantations before the start of treatment. Tumour fragments (about 25 mg) are implanted subcutaneously in the left flank of the animals using a 13-gauge trocar needle under Forene® anaesthesia (Abbott, Switzerland). Treatment with the test compound is started as soon as the tumour has reached a mean volume of 100 $mm^3$. Tumour growth is measured two to three times a week and 24 hours after the last treatment by determining the length of two perpendicular axes. The tumour volumes are calculated in accordance with published methods (see Evans et al., Brit. J. Cancer 45, 466-8 [1982]). The antitumour efficacy is determined as the mean increase in tumour volume of the treated animals divided by the mean increase in tumour volume of the untreated animals (controls) and, after multiplication by 100, is expressed as T/C %. Tumour regression (given in %) is reported as the smallest mean tumour volume in relation to the mean tumour volume at the start of treatment. The test compound is administered daily by gavage. In vivo tumor inhibition can e.g. be found at around 10 to 200 mg/kg and day.

As an alternative to cell line A-431, other cell lines may also be used in the same manner, for example the MCF-7 breast adenocarcinoma cell line, the MDA-MB 468 breast adenocarcinoma cell line, the MDA-MB 231 breast adenocarcinoma cell line, the Colo 205 colon carcinoma cell line, the HCT 116 colon carcinoma cell line, the DU145 prostate carcinoma cell line DU 145 or the PC-3 prostate carcinoma cell line PC-3

The inhibition of VEGF-induced KDR-receptor autophosphorylation can be confirmed with a further in vitro experiment in cells: transfected CHO cells, which permanently express human VEGF receptor (KDR), are seeded in culture medium (with 10% fetal calf serum=FCS) in 6-well cell-culture plates and incubated at 37° C. under 5% $CO_2$ until they show about 80% confluency. The compounds to be tested are then diluted in culture medium (without FCS, with 0.1% bovine serum albumin) and added to the cells. (Controls comprise medium without test compounds). After two hours' incubation at 37° C., recombinant VEGF is added; the final VEGF concentration is 20 ng/ml). After a further five minutes' incubation at 37° C., the cells are washed twice with ice-cold PBS (phosphate-buffered saline) and immediately lysed in 100 µl lysis buffer per well. The lysates are then centrifuged to remove the cell nuclei, and the protein concentrations of the supernatants are determined using a commercial protein assay (BIORAD). The lysates can then either be immediately used or, if desired, stored at −20° C.

A sandwich ELISA is carried out to measure the KDR-receptor phosphorylation: a monoclonal antibody to KDR (for example Mab 1495.12.14; prepared by H. Towbin) is immobilized on black ELISA plates (OptiPlate™ HTRF-96 from Packard). The plates are then washed and the remaining free protein-binding sites are saturated with 1% BSA in PBS.

The cell lysates (20 μg protein per well) are then incubated overnight at 4° C. with an antiphosphotyrosine antibody coupled with alkaline phosphatase (PY20:AP from Transduction Laboratories). The binding of the antiphosphotyrosine antibody is then demonstrated using a luminescent AP substrate (CDP-Star, ready to use, with Emerald II; TROPIX). The luminescence is measured in a Packard Top Count Microplate Scintillation Counter (Top Count). The difference between the signal of the positive control (stimulated with VEGF) and that of the negative control (not stimulated with VEGF) corresponds to VEGF-induced KDR-receptor phosphorylation (=100%). The activity of the tested substances is calculated as % inhibition of VEGF-induced KDR-receptor phosphorylation, wherein the concentration of substance that induces half the maximum inhibition is defined as the ED50 (effective dose for 50% inhibition). Compounds of formula I here preferably show ED50 values in the range of 5 nM to 10 μM. Those compounds where r is 1, Q is 4-lower alkoxy, especially lower methoxy, and is bound at A instead of the H, with A, B, D and E each being CH and T N, or preferably at T instead of the H, with T, B, D and E each being CH and A being A, and most especially those compounds wherein Q is oxo and one of the double bonds in the ring with A, B, D, E and T is a single bond, and the oxo Q is bound at A which is C if T is NH, while B, D and E each are CH, or preferably at T which is C if A is NH, while B, D and E each are CH, show especially advantageous inhibition.

Compounds of formula I inhibit to varying degrees also other tyrosine kinases involved in signal transduction which are mediated by trophic factors, for example Abl kinase, kinases from the Src family, especially c-Src kinase, Lck, and Fyn; or in a broader sense kinases of the EGF family, for example, c-erbB2 kinase (HER-2), c-erbB3 kinase, c-erbB4 kinase; insulin-like growth factor receptor kinase (IGF-1 kinase), especially members of the PDGF-receptor tyrosine kinase family, such as PDGF-receptor kinase, CSF-1-receptor kinase, Kit-receptor kinase and VEGF-receptor kinase, especially KDR and Flk, and the angiopoetin 1 and 2 receptor Tek; or in a broader sense also serine/threonine kinases, all of which play a role in growth regulation and transformation in mammalian cells, including human cells. The respective assays can be done utilizing the respective tyrosine kinase expressed as GST-fusion protein using the baculovirus system. The respective kinases are purified via a glutathione-Sepharose column and utilized to determine the $IC_{50}$s for the compounds.

The inhibition of c-erbB2 tyrosine kinase (HER-2) can be measured, for example, in the same way as the inhibition of EGF-R protein kinase (see House et al., Europ. J. Biochem. 140, 363-7 [1984]). The erbB2 kinase can be isolated, and its activity determined, using methods known per se (see Akiyama et al., Science 232, 1644 [1986]). In particular, an inhibitory effect can also be found on PDGF-receptor kinase, which is determined according to the method described by Trinks et al. (see J. Med. Chem. 37(7): 1015-27 [1994]).

The usefulness of a compound of the formula I in the treatment of arthritis as an example of an inflammatory rheumatic or rheumatoid disease can be demonstrated using the well-known rat adjuvant arthritis model (Pearson, Proc. Soc. Exp. Biol. 91, 95-101 (1956)) to test the anti-arthritic activity of compounds of the formula I (for details see WO 00/59509).

The activity of compounds of the formula I against pain can be shown in the model of nociception (pain) described also in WO 00/59509.

On the basis of these studies, a compound of formula I is appropriate for the treatment of inflammatory (especially rheumatic or rheumatoid) diseases and/or pain. The compounds of the formula I according to the invention also show therapeutic efficacy especially against other disorders dependent on protein kinase, especially proliferative diseases.

On the basis of their efficacy as inhibitors of VEGF-receptor tyrosine kinase activity, the compounds according to the invention primarily inhibit the growth of blood vessels and are thus, for example, effective against a number of diseases associated with deregulated angiogenesis, especially diseases caused by ocular neovascularisation, especially retinopathies, such as diabetic retinopathy or age-related macula degeneration, psoriasis, haemangioblastoma, such as haemangioma, mesangial cell proliferative disorders, such as chronic or acute renal diseases, e.g. diabetic nephropathy, malignant nephrosclerosis, thrombotic microangiopathy syndromes or transplant rejection, or especially inflammatory renal disease, such as glomerulonephritis, especially mesangioproliferative glomerulonephritis, haemolyticuraemic syndrome, diabetic nephropathy, hypertensive nephrosclerosis, atheroma, arterial restenosis, autoimmune diseases, acute inflammation, fibrotic disorders (e.g. hepatic cirrhosis), diabetes, neurodegenerative disorders and especially neoplastic diseases (solid tumours, but also leucemias and other "liquid tumours", especially those expressing c-kit, KDR or flt-1), such as especially breast cancer, cancer of the colon, lung cancer (especially small-cell lung cancer), cancer of the prostate or Kaposi's sarcoma. A compound of formula I inhibits the growth of tumours and is especially suited to preventing the metastatic spread of tumours and the growth of micrometastases.

A compound of formula I can be administered alone or in combination with one or more other therapeutic agents, possible combination therapy taking the form of fixed combinations or the administration of a compound of the invention and one or more other therapeutic agents being staggered or given independently of one another, or the combined administration of fixed combinations and one or more other therapeutic agents. In particular, a compound of formula I can besides or in addition be administered for example in the case of tumour therapy in combination with chemotherapy, radiotherapy, immunotherapy, surgical intervention, or a combination of these. Long-term therapy is equally possible as is adjuvant therapy in the context of other treatment strategies, as described above. Other possible treatments are therapy to maintain the patient's status after tumour regression, or even chemopreventive therapy, for example in patients at risk.

Therapeutic agents for possible combination are especially one or more antiproliferative, cytostatic or cytotoxic compounds, for example a chemotherapeutic agent or several agents selected from the group which includes, but is not limited to, an inhibitor of polyamine biosynthesis, an inhibitor of a protein kinase, especially of a serine/threonine protein kinase, such as protein kinase C, or of a tyrosine protein kinase, such as the EGF receptor tyrosine kinase, e.g. PKI166, the VEGF receptor tyrosine kinase, e.g. PTK787, or the PDGF receptor tyrosine kinase, e.g. STI571, a cytokine, a negative growth regulator, such as TGF-β or IFN-β, an aromatase inhibitor, e.g. letrozole or anastrozole, an inhibitor of the interaction of an SH2 domain with a phosphorylated protein, antiestrogens, topoisomerase I inhibitors, such as irinotecan, topoisomerase II inhibitors, microtubule active agents, e.g. paclitaxel, discodermolide or an epothilone, alkylating agents, antineoplastic antimetabolites, such as gemcitabine or capecitabine, platin compounds, such as carboplatin or cisplatin, anti-angiogenic compounds, gonadorelin agonists, anti-androgens, bisphosphonates, e.g. AREDIA® or ZOMETA®, and trastuzumab. The structure of the active agents identified by code nos., generic or trade names may be taken from the actual edition of the standard compendium "The Merck Index" or from databases, e.g. Patents International (e.g. IMS World Publications). The corresponding content thereof is hereby incorporated by reference.

The compounds of formula I, especially those wherein Q is oxo and r is preferably one, are especially appropriate for combination therapy and show especially low interference with other xenobiotics from e.g. food or especially drug administration as they display the advantage of low inhibition of metabolising enzymes, especially monooxygenases, preferably the CyP 450-dependent monooxygenases.

This can be shown according to the following test system: Human liver microsomes or high level expression of cDNAs encoding Cytochrome P450 in insect cells provide a flexible source of materials for several in vitro measurement methods. A microtiter plate-based, direct fluorometric assay for the activities of any one or more of the principal drug metabolizing enzymes CYP1A2, CYP2C8, CYP2C9, CYP2C19, CYP2D6 and/or CYP3A4 is used in order to assess the potential for drug candidates to inhibit cytochrome P450.

Fluorescent marker substrates are incubated at concentrations close to their Michaelis-Menten affinity constant, Km. Inhibitors are tested in the 1 to 10 µM concentration range. 50% inhibition concentration (IC50 values) are estimated by non-linear regression of a two parameter model equation where the lower data limit is 0, i.e. the data are background corrected, and the upper data limit is 100, i.e. the data are range corrected. The equation assumes that y falls with increasing x. A relatively high standard error associated with IC50 values suggests that the regression does not fit the data very well. Extrapolation or interpolation of IC50 values beyond the concentration range studied are not provided. The potential drug interaction is predicted with the following criterion: If the estimated apparent IC50 used is less than 1 µmol/l, the test compound has a potential drug interaction which should be investigated in more detail, if, on the other hand, the estimated IC50 is greater than 1 µmol/l, the test compound has a potential for drug interactions only if human therapeutic in vivo concentrations are likely to be in the IC50 range.

Details for the assays and the technology that forms the basis for the assays are known (see C. L. Crespi et al., Analytical Biochemistry 248, 188-190 (1997), and CIL. Crespi et al., J. Pharmacol. Toxicol. Methods 44, 325-331 (2000), and the references mentioned therein). For example, 3-cyano-7-ethoxycoumarin is used as fluorescent substrate for CYP1A2, CYP2C9, CYP2C19 and CYP2D6, 7-methoxy-4-trifluoromethylcoumarin is used for CYP2C9, resorufin benzyl ether for CYP3A4, 3-82-(N,N-diethyl-N-methylammonium)ethyl]-7-methoxy-4-methylcoumarin for CYP2D6.

With this test system, it can be shown that the compound of formula I, salts, tautomers or tautomer mixtures thereof show lower inhibition of CyP 450 isoenzymes; e.g. in the case of CyP 3A4, CyP2C8 and CyP2C9, a compound without substituent Q shows a higher inhibition by a factor of 2 or more when compared with a compound bearing an alkoxy or especially an oxo substituent, usually with 1 µM or higher IC50.

A compound of formula I is not only useful for the (prophylactic and preferably therapeutic) management of humans, but also for the treatment of other warm-blooded animals, for example of commercially useful animals, for example rodents, such as mice, rabbits or rats, or guinea-pigs. Such a compound may also be used as a reference standard in the test systems described above to permit a comparison with other compounds. In general, the invention relates also to the use of a compound of formula I for the inhibition of VEGF-receptor tyrosine kinase activity. A compound of formula I may also be used for diagnostic purposes, for example with tumours that have been obtained from warm-blooded animal "hosts", especially humans, and implanted into mice to test them for decreases in growth after treatment with such a compound, in order to investigate their sensitivity to said compound and thus to improve the detection and determination of possible therapeutic methods for neoplastic diseases in the original host.

With the groups of preferred compounds of formula I mentioned hereinafter, definitions of substituents from the general definitions mentioned hereinbefore may reasonably be used, for example, to replace more general definitions with more specific definitions or especially with definitions characterized as being preferred; in each case, the definitions described hereinbefore as being preferred or exemplary are preferred.

The present invention pertains in particular to compounds of the formula I wherein r is 1 or 2, n is 0 to 3, t is 0, $R_1$ and $R_2$ a) are independently in each case a lower alkyl;

b) together form a bridge of subformula I*, wherein the bond is achieved via the two terminal C atoms and m is 0 to 4, or c) together form a bridge of subformula I**, wherein one or two of the ring members $T_1$, $T_2$, $T_3$ and $T_4$ are nitrogen, and the others are in each case CH, and the bond is achieved via atoms $T_1$ and $T_4$;

G is —C(=O)—, —CHF—, —CF$_2$—, lower alkylene, $C_2$-$C_6$alkenylene, lower alkylene or $C_3$-$C_6$alkenylene substituted by acyloxy or hydroxy, —CH$_2$—O—, —CH$_2$—S—, —CH$_2$—NH—, —CH$_2$—O—CH$_2$—, —CH$_2$—S—CH$_2$—, —CH$_2$—NH—CH$_2$—, oxa (—O—), thia (—S—), imino (—NH—), —CH$_2$—O—CH$_2$—, —CH$_2$—S—CH$_2$—, —CH$_2$—NH—CH$_2$—, —(C(R$_4$)$_2$)$_t$—S(O)$_p$-(5-membered heteroaryl)-(C(R$_4$)$_2$)$_s$—, —(C(R$_4$)$_2$)$_t$—C(G$_1$)(R$_4$)—(C(R$_4$)$_2$)$_s$—, —O—CH$_2$—, —S(O)—, —S(O$_2$)—, —SCH$_2$, —S(O)CH$_2$—, —CH$_2$S(O)— or —CH$_2$S(O)$_2$—, wherein each of p, s and t, independently of the other, is 0, 1 or 2; R$_4$ is hydrogen, halogen or lower alkyl; and G$_1$ is —CN, —CO$_2$R$_3$, —CON(R$_6$)$_2$ or CH$_2$N(R$_6$)$_2$, wherein R$_3$ is hydrogen or lower alkyl and R$_6$ is hydrogen, alkyl, aryl or aryl-lower alkyl;

A, B, D, E and T are independently N or CH subject to the proviso that at least one and not more than three of these radicals are N;

Q is either lower alkoxy or O (oxo), with the proviso that if Q is lower alkoxy, the waved line representing the bonding of Q is a single bond and the ring carrying Q has three double bonds, and if Q is O, the waved line representing the bonding of Q is a double bond and for each Q=O, one of the double bonds in the ring is changed to a single bond; and with the proviso that any Q is bonded to a ring C atom;

$R_a$ and $R_a'$ are each independently H, halogen or lower alkyl;

X is imino, oxa, or thia;

Y is hydrogen, aryl, heteroaryl, or unsubstituted or substituted cycloalkyl; and Z is mono- or disubstituted amino, halogen, alkyl, cycloalkyl, substituted alkyl, hydroxy, etherified or esterified hydroxy, nitro, cyano, carboxy, esterified carboxy, —OCOR$_6$, —CH$_2$OR$_3$, —OCO$_2$R$_3$, alkanoyl, carbamoyl, N-mono- or N,N-disubstituted carbamoyl, amidino, guanidino, mercapto, sulfo, alkylthio, especially lower alkylthio, halogenated lower alkylthio, arylthio, especially phenylthio or alkylphenylthio, aryl lower alkylthio, especially phenyl lower alkylthio, arylsulfinyl, especially phenylsulfinyl or alkylphenylsulfinyl, aryl-lower alkylsulfinyl, especially phenyl-lower alkylsulfinyl, alkylsulfonyl, especially lower alkylsulfonyl, halogeno-lower alkylsulfonyl, arylsulfonyl, especially phenylsulfonyl or alkylphenylsulfonyl, aryl-lower alkylsulfonyl, especially phenyl-lower alkylsulfonyl, ureido, $C_2$-$C_7$alkenyl, aryl, heteroaryl, especially pyrazolyl or lower-alkyl pyrazolyl, optionally substituted saturated heterocyclyl, heteroarylalkyl, heteroaryloxy, —S(O)$_p$(heteroaryl) or —S(O)$_p$(heteroarylalkyl) wherein p is 0, 1 or 2, heteroaryloxy, —CHO or —OCON($R_6$)$_2$, —NR$_3$CO$_2$R$_6$ or —NR$_3$CON(R$_6$)$_2$ wherein $R_3$ and $R_6$ are as defined above; wherein—if more than 1 radical Z (m≧2) is present— the substituents Z are selected independently from each other, and wherein $R_3$ and $R_6$ are as defined above;

and wherein the bonds characterized in subformula I* by a wavy line are either single or double bonds;

with the proviso that when two groups $R_6$ are each alkyl and located on the same nitrogen atom, they may be linked by a bond, an O, an S or NR$_3$ with $R_3$ as defined above to form a N-containing heterocycle of 5 to 7 ring atoms;

and with the proviso that only compounds other than those wherein r is 1, n is 0, $R_1$ and $R_2$ together form a bridge of subformula I* wherein m is 0 and the waved lines represent double bonds, respectively, G is —CH$_2$—, T is N, each of A, B, E and T is CH, Q is methoxy and Y is 4-methyl-3-bromo-phenyl, 4-ethyl-3-bromo-phenyl, 3-chloro-5-trifluoromethyl-phenyl or 4-isopropyl-3-methyl-phenyl fall under the claim;

to the N-oxides of such compounds of formula I, wherein 1 or more N atoms carry an oxygen atom;

to the tautomers or mixtures of tautomers of such compounds of formula I and the N-oxides thereof;

and to the pharmaceutically acceptable salts of such compounds of formula I, of an N-oxide and of the tautomers and mixtures of tautomers thereof.

Preferred is a compound of formula I, wherein Q is O, with the proviso that the waved line representing the bonding of Q is a double bond and for each Q=O, one of the double bonds in the ring is changed to a single bond; and with the proviso that any Q is bonded to a ring C atom; and the other symbols have the meaning described for compounds of formula I above; an N-oxide of said compound of formula I, wherein 1 or more N atoms carry an oxygen atom; or a tautomer or mixture of tautomers of said compound of formula I or an N-oxide thereof; or a pharmaceutically acceptable salt of said compound of formula I, of an N-oxide or of a tautomer or mixture of tautomers thereof.

More preferred is a compound of formula I, wherein r is 1 or 2, preferably 1, t is 0, 1 or 2, n is 0, $R_1$ and $R_2$ together form a bridge of subformula I*, wherein the bond is achieved via the two terminal C atoms and m is 0, G is lower alkylene, especially methylene;

A, B, D, E and T are independently N or CH subject to the proviso that at least one and not more than three of these radicals are N;

Q is O, with the proviso that the waved line representing the bonding of Q is a double bond and for each Q=O, one of the double bonds in the ring is changed to a single bond; and with the proviso that any Q is bonded to a ring C atom;

Q' is halogen, NHR$^Q$, NR$^Q_2$, OR$^Q$, SR$^Q$, perfluoroalkyl, acyl, substituted or unsubstituted aryl, or substituted or unsubstituted hetaryl, wherein R$^Q$ represents acyl, alkyl, or alkyl substituted by hydroxy or halogen;

X is imino, oxa, or thia, preferably imino; and

Y is (i) hydrogen; (ii) phenyl which is either unsubstituted or substituted by one, two or three substituents selected independently of one another from the group consisting of halogen, especially fluorine, chlorine, bromine, or iodine; lower alkyl, especially methyl or preferably ethyl, further propyl or t-butyl; halogen-lower alkyl, especially trifluoromethyl; (iii) lower-alkyl-[1,3]dioxan-5-yl, such as cis, trans-, cis- or preferably trans-2-isopropyl-[1,3]dioxan-5-yl, heteroaryl, or unsubstituted or substituted cycloalkyl; or lower alkyl-cyclohexyl in cis, trans- cis- or preferably trans-form, preferably 4-isopropyl-cyclohexyl, especially in trans-form;

and wherein the bonds characterized in subformula I* by a wavy line are either single or double bonds, preferably both double bonds;

or an N-oxide of said compound of formula I, wherein 1 or more N atoms carry an oxygen atom;

or a tautomer or mixture of tautomers of said compound of formula I or an N-oxide thereof;

or a pharmaceutically acceptable salt of said compound of formula I, of an N-oxide or of a tautomer or mixture of tautomers thereof.

Still more preferred is a compound of formula I according to the preceding definitions wherein r is 1 and either T is NH, each of B, D and E is CH, A is C and Q is O bonded at A via a double bond, with the proviso that the double bond between A and T is absent;

or (especially preferably) A is NH, each of B, D and E is CH and T is C and Q is O bonded at T via a double bond;

and the remaining radicals and symbols are as defined above for compounds of formula for a tautomer or mixture of tautomers of said compound of formula I; or a pharmaceutically acceptable salt of said compound of formula I, of a tautomer or of a mixture of tautomers thereof.

One preferred embodiment of the invention relates to a compound of formula I wherein r is 1, n is 0, t is 0 or 1, $R_1$ and $R_2$ together form a bridge of subformula I*, wherein the bond is achieved via the two terminal C atoms and m is 0;

G is lower alkylene;

A, B, and E are CH;

D is CH and T is N or D is N and T is CH;

Q is either lower alkoxy or O (oxo), with the proviso that if Q is lower alkoxy, the waved line representing the bonding of Q is a single bond and the ring carrying Q has three double bonds, and if Q is O, the waved line representing the bonding of Q is a double bond and for each Q=O, one of the double bonds in the ring is changed to a single bond; and with the proviso that any Q is bonded to a ring C atom;

Q' is halogen, NHR$^Q$, wherein R$^Q$ represents lower alkyl; thiazolyl or furanyl;

X is imino or oxa;

Y is phenyl substituted by one or two substituents selected from lower alkyl, halogen and trifluoromethyl; $C_{5-7}$cycloalkyl, wherein up to two methylene groups are replaced by oxa, substituted by lower alkyl; or indolyl which is substituted by one or two substituents selected from lower alkyl and halogen;

and wherein the bonds characterized in subformula I* by a wavy line are double bonds;

and with the proviso that only compounds other than those wherein G is —CH$_2$—, T is N, each of A, B, E and T is CH, Q is methoxy and Y is 4-methyl-3-bromo-phenyl, 4-ethyl-3-bromo-phenyl, 3-chloro-5-trifluoromethyl-phenyl or 4-isopropyl-3-methyl-phenyl fall under the claim;

a tautomer or mixture of tautomers of a compound of formula I;

a pharmaceutically acceptable salt of a compound of formula I, of a tautomer or of a mixture of tautomers thereof.

Most preferred are the compounds given in the examples, especially those wherein Q is oxo (O), tautomers or mixtures of tautomers thereof; or salts of any of these A compound of the formula I may be prepared by processes known per se for other compounds, especially by or in analogy to any of the methods described in WO 98/35958, WO 00/59509 or WO 01/10859, which are therefore incorporated by reference herewith, especially for the preparation of a compound of formula I, in which G is —CH$_2$—, by reacting a compound of formula II,

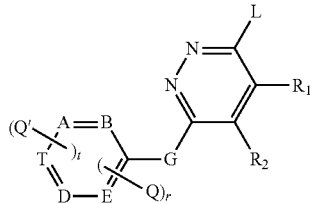

(II)

wherein Q, Q', A, B, D, E, T, R$_1$, and R$_2$ are as defined for a compound of formula I, G is —CH$_2$— and L is a nucleofugal leaving group, with a compound of formula III

(III)

wherein n, R$_a$, R$_a$', X, and Y are as defined for a compound of formula I;

wherein in compounds of formulae I, II and/or III functional groups which shall not participate in the reaction are present in protected form where necessary, and removing any protective groups present, whereas said starting compounds may also be present in the form of salts if a salt-forming group is present and the reaction in salt form is possible;

and, if so desired, converting an obtainable compound of formula I into another compound of formula I, converting a free compound of formula I into a salt, converting an obtainable salt of a compound of formula into the free compound or another salt, and/or separating a mixture of isomeric compounds of formula I thereof into the individual isomers, the term "compound of formula I" in the present paragraph being understood to be directed to the compounds of formula I, its N-oxides, and/or tautomers or mixtures of tautomers of any of these.

Detailed Description of Methods

In the more detailed description of the process method below, r, n, t, A, B, D, E, T, G, Q, Q', R$_a$, R$_a$', R$_1$, R$_2$, X and Y are as defined for compounds of formula I, unless otherwise indicated.

In the compound of formula II, a nucleofugal leaving group L is especially halogen, above all bromine, especially chlorine or iodine.

The reaction between the compound of formula II and the compound of formula III takes place in suitable, inert polar solvents, especially alcohols, e.g. lower alcohols, such as methanol, ethanol, propanol, isopropanol or n-butanol, in the presence of cyclic ethers, especially dioxane, or in the presence of mixtures of one or more alcohols with one or more cyclic ether, e.g. in isopropanol/dioxane mixtures; or in a melt without the addition of a solvent, especially if one of the reaction partners is present in liquid form. The reaction takes place at elevated temperatures, preferably between about 60° C. and the reflux temperature of the solvent used, for example under reflux conditions, or at a temperature between approximately 70 and approximately 150° C. (if necessary in a closed vessel). The compound of formula III may also be used as a salt, for example as an acid addition salt with a strong acid, such as a hydrogen halide, for example as a hydrochloride salt, or the corresponding acid, for example hydrochloric acid, can be added in a suitable solvent, for example an ether, such as dioxane. If L is iodine, the reaction is preferably allowed to proceed in presence or absence of an inert solvent, such as toluene, in the presence of a base, especially a nitrogen base, such as tributylamine, or an alkalimetal carbonate, such as dipotassium carbonate, in the presence of catalytic amounts of tetrakis-(triphenylphosphin)-palladium, at elevated temperature, e.g. at 80 to 115° C.

Additional Process Steps

In the additional process steps which are carried out as desired, functional groups of the starting compounds which should not take part in the reaction may be present in unprotected form or may be protected for example by one or more of the protecting groups mentioned hereinabove. The protecting groups are then wholly or partly removed according to one of the methods described.

If one or more other functional groups, for example carboxy, hydroxy, amino, or mercapto, are or need to be protected in a compound of formulae II or III, because they should not take part in the reaction, these are such as are usually used in the synthesis of peptide compounds, cephalosporins or penicillins, as well as nucleic acid derivatives and sugars. The protecting groups may already be present in precursors and should protect the functional groups concerned against unwanted secondary reactions, such as acylations, etherifications, esterifications, oxidations, solvolysis, and similar reactions. In certain cases, the protecting groups may, in addition to this protection, effect a selective, typically stereoselective, course of reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. A person skilled in the art knows, or can easily establish, which protecting groups are suitable with the reactions mentioned hereinabove and hereinafter.

The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene, "Protective Groups in Organic Synthesis", Wiley, New York 1981, in "The Peptides"; Volume 3 (editors: E. Gross and J. Meienhofer), Academic Press, London and New York 1981, in "Methoden der organischen Chemie" (*Methods of organic chemistry*), Houben Weyl, 4th edition, Volume 15/I, Georg Thieme Verlag, Stuttgart 1974, in H.-D. Jakubke and H. Jescheit, "Aminosäuren, Peptide, Proteine" (*Amino acids, peptides, proteins*), Verlag Chemie, Weinheim, Deerfield Beach, and Basel 1982, and in Jochen Lehmann, "Chemie der Kohlenhydrate: Monosaccharide and Derivate" (*Chemistry of carbohydrates: monosaccharides and derivatives*), Georg Thieme Verlag, Stuttgart 1974.

Salts of a compound of formula I (or an N-oxide, a tautomer or a mixture of tautomers thereof) with a salt-forming group may be prepared in a manner known per se. Acid addition salts may thus be obtained by treatment with an acid or with a suitable anion exchange reagent. A salt with two acid molecules (for example a dihalogenide of a compound of formula I (or an N-oxide, a tautomer or a mixture of tautomers thereof)) may also be converted into a salt with one acid molecule per compound (for example a monohalogenide); this may be done by heating to a melt, or for example by heating as a solid under a high vacuum at elevated temperature, for example from 130 to 170° C., one molecule of the acid being expelled per molecule of a compound according to the invention. Salts can usually be converted to free compounds, e.g. by treating with suitable basic agents, for example with alkali metal carbonates, hydrogencarbonates, or hydroxides, typically potassium carbonate or sodium hydroxide.

Stereoisomeric mixtures, e.g. mixtures of diastereomers, can be separated into their corresponding isomers in a manner known per se by means of suitable separation methods. Diastereomeric mixtures for example may be separated into their individual diastereomers by means of fractionated crystallization, chromatography, solvent distribution, and similar procedures. This separation may take place either at the level of one of the starting compounds or in a compound of formula I itself. Enantiomers may be separated through the formation of diastereomeric salts, for example by salt formation with an enantiomer-pure chiral acid, or by means of chromatography, for example by HPLC, using chromatographic substrates with chiral ligands.

A compound of formula I wherein Q is oxo is prepared from a compound wherein Q is lower alkoxy (obtainable by the process shown above or in analogy to the methods described in WO 98/35958, WO 00/59509 or WO 01/10859) by reacting a tri-lower alkylsilylhalogenide, especially -iodide, most preferably trimethylsilyl-iodide, in an appropriate solvent, especially a halogenated hydrocarbon, such as trichloromethane or methylenchloride, at elevated temperature, e.g. at a temperature between 30° C. and the reflux temperature, especially at 55 to 65° C., preferably with subsequent addition of a base, such as a nitrogen base or especially a metal carbonate or metal hydrogen carbonate, such as an alkali metal carbonate or -hydrogen carbonate, in a mixture of water, an alcohol, especially methanol, and an ester, especially a lower alkyl-alkanoate, preferably ethyl acetate, preferably at a temperature between 0 and 50° C., e.g. at ambient temperature. Other methods of ether cleavage can make use of Lewis acids, such as $BF_3$, $BCl_3$, $(CH_3)_2B$—Br, $BBr_3$ or $AlCl_3$ (see e.g. Jerry March, "Advanced Organic Chemistry—Reactions, Mechanisms and Structure", $4^{th}$ edition, Wiley-Interscience 1992), page 434, and references cited therein).

Other transformations of a compound of the formula I, an N-oxide, a tautomer or mixture of tautomers of any of these or a salt of any of these, respectively, can be made in analogy to the additional process steps described in WO 98/35958, WO 00/59509 or WO 01/10859, which are therefore incorporated by reference herewith.

General Process Conditions

All process steps described here can be carried out under known reaction conditions, especially those described as General process conditions in WO 98/35958 and WO 00/59509, which are therefore incorporated by reference herewith.

The invention relates also to those forms of the process in which one starts from a compound obtainable at any stage as an intermediate and carries out the missing steps, or breaks off the process at any stage, or forms a starting material under the reaction conditions, or uses said starting material in the form of a reactive derivative or salt, or produces a compound obtainable by means of the process according to the invention and processes said compound in situ. In the preferred embodiment, one starts from those starting materials which lead to the compounds described hereinabove as preferred, particularly as especially preferred, primarily preferred, and/or preferred above all.

In the preferred embodiment, a compound of formula I is prepared according to or in analogy to the processes and process steps defined in the Examples.

The compounds according to the invention, including their salts, are also obtainable in the form of hydrates, or their crystals can include for example the solvent used for crystallization (present as solvates).

Pharmaceutical Preparations, Methods, and Uses

The present invention relates also to pharmaceutical compositions that comprise a compound of formula I as active ingredient and that can be used especially in the treatment of the diseases mentioned at the beginning. Compositions for enteral administration, such as nasal, buccal, rectal or, especially, oral administration, and for parenteral administration, such as intravenous, intramuscular or subcutaneous administration, to warm-blooded animals, especially humans, are especially preferred. The compositions comprise the active ingredient (a compound of the formula I, ist N-oxide, tautomers or tautomer mixtures of any of these or a pharmaceutically acceptable salt of any of these) alone or, preferably, together with a pharmaceutically acceptable carrier. The dosage of the active ingredient depends upon the disease to be treated and upon the species, its age, weight, and individual condition, the individual pharmacokinetic data, and the mode of administration.

The invention relates also to pharmaceutical compositions for use in a method for the prophylactic or especially therapeutic management of the human or animal body, to a process for the preparation thereof (especially in the form of compositions for the treatment of tumours) and to a method of treating tumour diseases, especially those mentioned above, where a compound of the formula I is used.

The invention relates also to processes and to the use of compounds of formula I for the preparation of pharmaceutical preparations which comprise compounds of formula I as active component (active ingredient).

The said pharmaceutical preparations may also, if so desired, comprise other active components, for example cytostatic agents, and/or be used in combination with known therapeutic methods, for example the administration of hormones or irradiation.

Preference is for a pharmaceutical preparation which is suitable for administration to a warm-blooded animal, especially humans or commercially useful mammals suffering from an inflammatory rheumatoid or rheumatic disease and/or pain, or a disease which responds to an inhibition of angiogenesis or of VEGF-receptor tyrosine kinase, for example psoriasis or especially a neoplastic disease, comprising an effective quantity of a compound of formula I for the inhibition of angiogenesis or of VEGF-receptor tyrosine kinase, or a pharmaceutically acceptable salt thereof, if salt-forming groups are present, together with at least one pharmaceutically acceptable carrier.

A pharmaceutical composition for the prophylactic or especially therapeutic management of a rheumatoid or rheumatic inflammatory disease and/or pain, or a neoplastic and other proliferative disease of a warm-blooded animal, especially a human or a commercially useful mammal requiring such treatment, especially suffering from such a disease, comprising as active ingredient in a quantity that is prophylactically or especially therapeutically active against said diseases a new compound of formula I, is likewise preferred.

The pharmaceutical compositions comprise from approximately 1% to approximately 95% active ingredient, single-dose administration forms comprising in the preferred embodiment from approximately 20% to approximately 90% active ingredient and forms that are not of single-dose type comprising in the preferred embodiment from approximately 5% to approximately 20% active ingredient. Unit dose forms are, for example, coated and uncoated tablets, ampoules, vials, suppositories, or capsules. Examples are capsules containing from about 0.05 g to about 1.0 g of active substance.

The pharmaceutical compositions of the present invention are prepared in a manner known per se, for example by means of conventional mixing, granulating, coating, dissolving or lyophilizing processes.

Pharmaceutical compositions for oral administration can be obtained, for example, by combining the active ingredient with one or more solid carriers, if need be granulating a resulting mixture, and processing the mixture or granules, if desired, to form tablets or tablet cores, if need be by the inclusion of additional excipients.

Suitable carriers are especially fillers, such as sugars, cellulose preparations, and/or calcium phosphates, and also binders, such as starches, methylcellulose, and/or polyvinylpyrrolidone, and/or disintegrators. Additional excipients are especially flow conditioners and lubricants, for example silicic acid, talc, stearic acid or salts thereof and/or polyethylene glycol, or derivatives thereof.

Tablet cores may be provided with suitable coatings. Orally administrable pharmaceutical compositions also include hard capsules consisting of gelatin, and also soft, sealed capsules consisting of gelatin and a plasticiser, such as glycerol or sorbitol. In soft capsules, the active ingredient is preferably dissolved or suspended in suitable liquid excipients, such as fatty oils.

Suitable rectally administrable pharmaceutical compositions are, for example, suppositories that consist of a combination of the active ingredient and a suppository base.

The aqueous solutions suitable for parenteral administration are especially those of an active ingredient in water-soluble form, for example in the form of a water-soluble salt, or aqueous injection suspensions that contain viscosity-increasing substances. Solutions such as are used for parenteral administration can also be employed as infusion solutions.

The invention relates likewise to a process or a method for the treatment of one of the pathological conditions mentioned hereinabove, especially an inflammatory rheumatic or rheumatoid disease and/or pain, or a disease which responds to an inhibition of the VEGF-receptor tyrosine kinase or an inhibition of angiogenesis, especially a corresponding neoplastic disease or also psoriasis. The compounds of formula I can be administered as such or in the form of pharmaceutical compositions, prophylactically or therapeutically, preferably in an amount effective against said diseases, to a warm-blooded animal, for example a human, requiring such treatment, the compounds especially being used in the form of pharmaceutical compositions. In the case of an individual having a body weight of about 70 kg the daily dose administered is from approximately 0.1 g to approximately 5 g, preferably from approximately 0.5 g to approximately 2 g, of a compound of formula I.

The present invention relates especially also to the use of a compound of formula I (in this paragraph meaning the compound of formula I, an N-oxide thereof, or a tautomer or tautomeric mixture of any of these), or a pharmaceutically acceptable salt thereof, especially a compound of formula I which is said to be preferred, or a pharmaceutically acceptable salt thereof, as such or in the form of a pharmaceutical formulation with at least one pharmaceutically acceptable carrier for the therapeutic and also prophylactic management of one or more of the diseases mentioned hereinabove, preferably an inflammatory rheumatic or rheumatoid disease and/or pain, or especially a disease which responds to an inhibition of VEGF-receptor tyrosine kinase or an inhibition of angiogenesis, especially a neoplastic disease or also psoriasis, above all if said disease responds to an inhibition of VEGF-receptor tyrosine kinase or angiogenesis.

The present invention relates especially also to the use of a compound of formula I as defined in the last paragraph, or a pharmaceutically acceptable salt thereof, especially a compound of formula I which is said to be preferred, or a pharmaceutically acceptable salt thereof, for the preparation of a pharmaceutical formulation for the therapeutic and also prophylactic management of one or more of the diseases mentioned hereinabove, especially a rheumatic or rheumatoid inflammatory disease and/or pain, or especially a neoplastic disease or also psoriasis, above all if the disease responds to an inhibition of VEGF-receptor tyrosine kinase or angiogenesis. The preferred dose quantity, composition, and preparation of pharmaceutical formulations (medicines) to be used in each case are described above.

Starting Materials

New starting materials and/or transients, as well as processes for the preparation thereof, are likewise the subject of this invention. In the preferred embodiment, such starting materials are used and reaction conditions so selected as to enable the preferred compounds to be obtained.

The starting materials of formulae II and III are known, capable of being prepared according to known processes, or commercially obtainable; in particular, they can be prepared using processes as described in the Examples.

In the preparation of starting materials, existing functional groups which do not participate in the reaction should, if necessary, be protected. Preferred protecting groups, their introduction and their removal are described hereinabove or in the Examples. In place of the respective starting materials and transients, salts thereof may also be used for the reaction, provided that salt-forming groups are present and the reaction with a salt is also possible. Where the term starting materials is used hereinbefore and hereinafter, the salts thereof are always included, insofar as reasonable and possible.

A compound of formula II, wherein G is —CH$_2$— and the remaining symbols are as defined under formula I, can be prepared for example by reacting an aldehyde of formula IV,

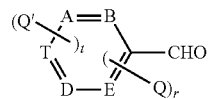

(IV)

wherein Q is lower alkoxy and A, B, D, E, Q', T, t and r are as defined for compounds of formula I, with a triphenylphosphonium-halide, especially -chloride, of the formula V,

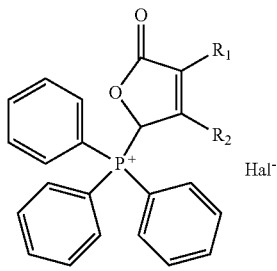

(V)

wherein $R_1$ and $R_2$ are as defined for a compound of formula I and Hal is halogen, especially Cl, in the presence of an appropriate solvent, e.g. an ether, especially tetrahydrofurane, and a tertiary amine, especially triethylamine, preferably at lowered temperature, e.g. between −10 and 15° C., resulting in a lactone compound of the formula VI,

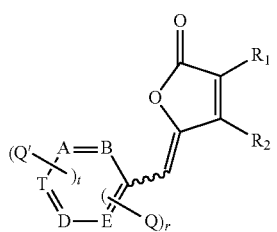

(VI)

wherein $R_1$, $R_2$, A, B, D, E, Q', T, t and r have the meanings given under formula I and Q is lower alkoxy, which compound is then converted by reaction with hydrazine (preferably in the form of ist hydrate), preferably in the presence of a solvent or solvent mixture, such as a cyclic ether, especially tetrahydrofuran, and/or water, at an elevated temperature, preferably between 50° C. and reflux temperature, to the corresponding phthalazine analogue of the formula VII,

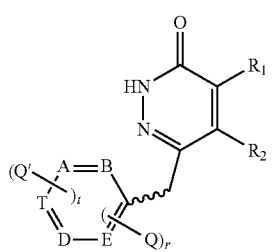

(VII)

wherein the symbols are as defined for compounds of the formula VI; the compound of formula VII is then be converted to the corresponding compound of formula II, wherein L is halogen, especially chlorine, G is methylene, and the remaining radicals are as defined under formula I, by reaction with a phosphoryl halide or phosphorus pentahalide, especially phosphoryl chloride ($POCl_3$) or phosphorus pentachloride without solvent or in a suitable solvent, for example acetonitrile, at preferred temperatures between 40° C. and reflux temperature, preferably under reflux, preferably in the presence of the respective hydrohalic acid, e.g. HCl. Instead of halogen L, another nucleofugal radical (e.g. tosyl) can be introduced by substitution under customary conditions The starting materials of formula IV are known, capable of being prepared according to known processes, or commercially obtainable; in particular, they can be prepared using processes in analogy to those described in the Examples.

Other starting materials are known, capable of being prepared according to known processes, or commercially available; in particular, they can be prepared using processes identical or analogous to those described in the Examples.

EXAMPLES

The subsequent examples serve for illustrating the invention without limiting the scope thereof. Temperatures are represented in degree Celsius (° C.). If not mentioned otherwise, reactions take place at room temperature.

HPLC-Gradient:
Grad$_{20\text{-}100}$ 20%→100% a) in b) during 13 min+5 min 100% a).
Grad$_{5\text{-}40}$ 5%→40% a) in b) during 9 min+7 min 40% a).
Eluent a): Acetonitrile+0.05% TFA; Eluent b): Water+0.05% TFA. Column (250×4.6 mm) filled with reversed-phase-material C18-Nucleosil (5 μm mean bead diameter, silicagel covalently modified with octadecylsilanes, Macherey & Nagel, Düren, BRD). Detection: UV-absorption at 215 nm. Retention times ($t_{Ret}$) are represented in minutes. Flow rate 1 ml/min.

The further short names and abbreviations used have the following meanings:
Ex. example
DIPE di-isopropyl-ether
DMF dimethylformamid
DMSO dimethylsulfoxide
ES-MS "Elektron Spray" mass spectroskopie
Ether diethylether
EtOAc ethyl acetate
FAB-MS "Fast Atom Bombardement" mass spectroskopie
sat. saturated
h hour(s)
min minute(s)
RT room temperature
RE rotary evaporator
m.p. Melting point
brine saturated sodium chloride solution
TFA trifluoroacetic acid
THF tetrahydrofurane (dest. over Na/benzophenone)

Example 1 trans 1-(4-Isopropyl-cyclohexylamino)-4-[2-hydroxy-(pyridin-4-yl)-methyl]-phthalazine Under $N_2$-atmosphere, 0.28 ml (2.05 mMol) $Me_3SiI$ are added to 400 mg (1.02 mMol) of trans 1-(4-isopropyl-cyclohexylamino)-4-[2-methoxy-(pyridin-4-yl)-methyl]-phthalazine in 10 ml chloroform, and the resulting mixture is stirred during 20 h at 60° C. After cooling to RT, 5 ml sat. $NaHCO_3$-solution, 5 ml water, 20 ml EtOAc and a small amount of methanol are added, followed by agitation. The resulting white crystals are filtered off, washed with water and dried, yielding the title compound: M.p. 266-267° C. (decomposition); FAB-MS: $(M+H)^+$=377; HPLC(Grad$_{20\text{-}100}$) $t_{Ret}$=10.3). From the filtrate, by extraction with EtOAc, washing of the organic phase with water and brine, drying ($Na_2SO_4$), evaporation and crystallisation from dichlormethane/methanol under addition of ether, more product results.

The starting materials are prepared as follows:

1a) 3-[1-(2-Methoxy-pyridin-4-yl)-methyliden]-3.H.-isobenzofuran-1-one

Under exclusion of air, 4.6 g (10.7 mMol) of 1,3-dihydro-3-oxo-1-isobenzofuranyl-triphenyl-phosphonium chloride (preparation see *J. Organomet. Chem.* 1972, 42, 391) and 1.85 ml (13 mMol) triethylamine are added to an ice-cooled solution of 1.75 g (12.8 mMol) 2-methoxy-pyridin-4-carbaldehyde (preparation see *Eur. J. Med. Chem.* 1993, 28, 601) in 29 ml THF. After stirring for 2 h in the ice bath, the mixture is suction-filtered, the remainder is washed out with EtOAc and the filtrate is evaporated yielding the title compound (mixture of the double bond isomers, further containing triphenyl phosphinoxide): HPLC(Grad$_{20-100}$) t$_{Ret}$=12.1/12.6

1b) 4-[2-Methoxy-pyridin-4-yl)methyl]phthalazin-1 (2H)-one 4.4 g (17 mMol) 3-[1-(2-methoxy-pyridin-4-yl)-methyliden]-3.H.-isobenzofuran-1-one in 60 ml THF and 60 ml hydrazine-hydrate are stirred during 75 min under reflux. After cooling to RT, the mixture is diluted with water and EtOAc, and the aqueous phase is separated off and extracted twice with EtOAc. The organic phases are extracted three times each with 26 ml 1 N HCl, and the acidic aqueous phases are made alkaline with 1 N NaOH and extracted three times with EtOAc. The EtOAc extracts are washed twice with water and brine, dried (Na$_2$SO$_4$) and partially evaporated in a RE. Under agitation, the title compound crystallizes out from the residue and is filtered off: FAB-MS: (M+H)$^+$=268; HPLC (Grad$_{20-100}$) t$_{Ret}$=7.9.

1c) 1-Chloro-4-[2-methoxy-pyridin-4-yl)methyl] phthalazine

Under exclusion of humidity, 1.7 ml (19 mMol) phosphorous oxychloride and 3.8 ml 4 N HCl in dioxane are added to 2.0 g (7.5 mMol) 4-[2-methoxy-pyridin-4-yl)methyl]phthalazin-1(2H)-one in 40 ml of acetonitrile. After 15 h of agitation at 65° C., the mixture is cooled, and the precipitate is filtered off and is washed with acetonitrile*. The residue is dissolved in 25 ml of water, and 15 ml of 2.5% NH$_3$ solution are added. The title compound precipitating in the course of this is filtered off, washed with water, dried, redissolved in THF and crystallized by addition of hexane.: M.p. 105-106° C.; FAB-MS: (M+H)$^+$=286. *From the filtrate, by distribution between EtOAc, 2.5% NH$_3$ solution, water and brine, further product can be obtained.

1d) trans 1-(4-Isopropyl-cyclohexylamino)-4-[2-methoxy-(pyridin-4-yl)-methyl]-phthalazine Under N$_2$ atmosphere, in an ampoule 1.73 g (12 mMol) of trans 4-isopropyl-cyclohexylamine (preparation see *Arzneim. Forsch.* 1969, 19, 140) and 700 mg (2.4 mMol) of 1-chloro-4-[2-methoxy-pyridin-4-yl)methyl]phthalazine are heated during 17 h at 140° C. The reaction mixture is suspended in EtOAc, and 1.5 ml of NH$_3$ solution (25%) and water are added. The isolated aqueous phase is extracted another two times with EtOAc, and the organic phases are washed with water and brine, dried (Na$_2$SO$_4$) and evaporated to dryness. Column chromatography (SiO$_2$; hexane/EtOAc 1:1) results in the title compound: M.p. 65-66° C.; FAB-MS: (M+H)$^+$=391.

Example 2

1-(3-Bromo-4-ethyl-anilino)-4-[2-hydroxy-(pyridin-4-yl)-methyl]phthalazine

In analogy to Ex. 1, 500 mg (1.11 mMol) of 1-(3-bromo-4-ethyl-anilino)-4-[2-methoxy-(pyridin-4-yl)-methyl]-phthalazine in 12 ml of chloroform are reacted with 0.3 ml (2.2 mMol) Me$_3$Sil to give the title compound: M.p. 251-252° C.; FAB-MS: (M+H)$^+$=435/437; HPLC(Grad$_{20-100}$) t$_{Ret}$=9.6.

The starting materials are prepared as follows:

2a) 3-Bromo-4-ethyl-aniline

Obtained by hydrogenation of 4.45 g (19 mMol) of 3-bromo-4-ethyl-nitrobenzene (preparation see *Macromolecules* 1995, 28, 5618) in 100 ml of ethanol in the presence of 1 g Raney nickel, filtration, evaporation and column chromatography (SiO$_2$; methylenchloride): $^1$H NMR (CDCl$_3$) δ 6.94 (d, 1H), 6.82 (s, 1H), 6.50 (d, 1H), 3.50 (s, H$_2$N), 2.57 (q, 2H), 1.10 (t, 3H).

2b) 1-(3-Bromo-4-ethyl-anilino)-4-[2-methoxy-(pyridin-4-yl)-methyl]-phthalazine Under N$_2$-atmosphere, 0.73 g (3.7 mMol) 3-bromo-4-ethyl-aniline and 0.82 ml 4 N HCl/dioxane are added to 1.00 g (3.5 mMol) 1-chloro-4-[2-methoxy-pyridin-4-yl)methyl] phthalazine in 12 ml methanol, and the mixture is stirred for 2 h at 70° C. After cooling, the resulting yellow solution is diluted with EtOAc and 2.5% NH$_3$ solution, and the aqueous phase is removed and extracted twice with EtOAct. The organic phases are washed with water and brine, dried (Na$_2$SO$_4$) and evaporated with a RE. After addition of DIPE to the residue, the title compound crystallizes out: M.p. 133-135° C.; FAB-MS: (M+H)$^+$=449/451; HPLC(Grad$_{20-100}$) t$_{Ret}$=11.4.

Example 3

1-(4-tert-Butyl-anilino)-4-[6-hydroxy-(pyridin-3-yl)-methyl]-phthalazine

Under protective gas, 0.37 ml (2.6 mMol) of Me$_3$Sil are added to 500 mg (1.3 mMol) of 1-(4-tert-butyl-anilino)-4-[6-methoxy-(pyridin-3-yl)-methyl]-phthalazine in 15 ml of chloroform, and the mixture is stirred during 6 h at 60° C. After cooling to RT, 20 ml of sat. NaHCO$_3$ solution, 10 ml of water, 200 ml of EtOAc and a small amount of methanol are added, followed by agitation until all is dissolved. The aqueous phase is removed and extracted twice with EtOAc. The organic phases are washed with water and brine, dried (Na$_2$SO$_4$) and evaporated partially with a RE. During this procedure, the title compound crystallizes out: M.p. 277-278° C. (decomposition); FAB-MS: (M+H)$^+$=385; HPLC (Grad$_{20-100}$) t$_{Ret}$=9.8.

The starting materials are prepared as follows:

3a) 6-Methoxy-pyridin-3-carbaldehyde 10 g (71.9 mMol) of 2-methoxy-5-hydroxymethylpyridine (preparation see *Heterocycl. Commun.* 1999, 5, 257) are dissolved in 160 ml of DMSO and 30 ml (215 mMol) of triethylamine. At RT (exothermic-cool!), 34.3 g (215 mMol) of sulfur trioxide pyridine complex in 160 ml DMSO are added dropwise, and the mixture is stirred 1 h at RT. The mixture is poured into water and extracted three times with EtOAc. The organic phases are washed with water and brine, dried ($Na_2SO_4$) and evaporated to yield the title compound: HPLC ($Grad_{5-40}$) $t_{Ret}$=12.9.

3b) 3-[1-(6-Methoxy-pyridin-3-yl)-methyliden]-3.H.-isobenzofuran-1-one

Under exclusion of air, 38.7 g (89.8 mMol) of 1,3-dihydro-3-oxo-1-isobenzofuranyl-triphenyl-phosphonium chloride (preparation see *J. Organomet. Chem.* 1972, 42, 391) and 11 ml (79 mMol) of triethylamine are added to an ice-cooled solution of 9.9 g (72 mMol) of 6-methoxy-pyridin-3-carbaldehyde in 150 ml THF. After stirring 2 h on the ice bath, the mixture is filtrated, the residue is washed out with EtOAc and the filtrate is evaporated, yielding the double bond isomers of the title compound, further containing triphenyl phosphinoxide): FAB-MS: $(M+H)^+$=254.

3c) 4-[6-Methoxy-pyridin-3-yl)methyl]phthalazin-1(2H)-one 38.9 g of the raw 3-[1-(6-methoxy-pyridin-3-yl)-methyliden]-3.H.-isobenzofuran-1-one just mentioned in 400 ml of THF and 400 ml of hydrazine hydrate are stirred for 90 min at 80° C. After cooling to RT, the mixture is diluted with 1.5 l of water and 1 l of EtOAc, and the water phase is removed and extracted a further two times with EtOAc. The organic phases are washed with water and then extracted three times each with 400 ml of 1 N HCl, and the acidic aqueous phases are made alkaline with 4 N NaOH and extracted three times each with 400 ml EtOAc. The resulting EtOAc extracts are washed with water and brine, dried ($Na_2SO_4$) and evaporated partially using a RE. During that procedure, the title compound crystallizes out and is obtained by filtration: FAB-MS: $(M+H)^+$=268; HPLC($Grad_{20-100}$) $t_{Ret}$=7.7.

3e) 1-Chloro-4-[6-methoxy-pyridin-3-yl)methyl]phthalazine

Excluding humidity, 13 ml (142 mMol) of phosphorous oxychloride and 20 ml of 4 N HCl in dioxane are added to 10.8 g (40 mMol) of 4-[6-methoxy-pyridin-3-yl)methyl]phthalazin-1(2H)-one in 170 ml of acetonitrile. After stirring for 24 h at 75° C., the mixture is cooled, and the precipitate is filtered off and washed out with acetonitrile*. The residue is dissolved in 150 ml of water, and 170 ml of 2.5% $NH_3$ solution are added. The precipitate forming during that procedure is re-dissolved by addition of EtOAc, and the aqueous phase is removed and extracted twice with EtOAc. The organic phases are washed with water and brine, dried ($Na_2SO_4$) and evaporated partially with a RE. This caused the title compound to crystallize out, which is filtered off: M.p. 134-135° C.; FAB-MS: $(M+H)^+$=286. *From the filtrate, by distribution between EtOAc, 2.5% $NH_3$ solution, water and brine and column chromatography ($SiO_2$; methylenchloride→methylenchloride/EtOAc 9:1→7:3→EtOAc) further product is obtained.

3f) 1-(4-tert-Butyl-anilino)-4-[6-methoxy-(pyridin-3-yl)-methyl]-phthalazine Under $N_2$ atmosphere, 0.40 g (2.7 mMol) of 4-tert-butyl-aniline and 0.62 ml 4 N HCl/dioxane are added to 750 mg (2.6 mMol) of 1-chloro-4-[6-methoxy-pyridin-3-yl)methyl]phthalazine in 11 ml of methanol, and the mixture is stirred for 2 h at 65° C. After cooling, the resulting yellow solution is diluted with EtOAc, 20 ml of water and 10 ml of 2.5% $NH_3$ solution, and the aqueous phase is removed and extracted twice with EtOAc. The organic phases are washed with water and brine, dried and partially evaporated with a RE. After addition of DIPE to the remnant, the title compound crystallizes out: FAB-MS: $(M+H)^+$=399; HPLC($Grad_{20-100}$) $t_{Ret}$=11.9.

Example 4 trans 1-(4-Isopropyl-cyclohexylamino)-4-[6-hydroxy-(pyridin-3-yl)-methyl]-phthalazine Under $N_2$ atmosphere, 0.35 ml (2.6 mMol) of $Me_3SiI$ are added to 500 mg (1.3 mMol) of trans 1-(4-isopropyl-cyclohexylamino)-4-[6-methoxy-(pyridin-3-yl)-methyl]-phthalazine in 15 ml of chloroform, followed by stirring for 16 h at 60° C. After cooling to RT, 15 ml of sat. $NaHCO_3$ solution, 10 ml of water, EtOAc and a small amount of methanol are added, followed by agitation. From the resulting solution, the aqueous phase is removed and extracted twice with EtOAc. The organic phases are washed with water and brine, dried ($Na_2SO_4$) and evaporated to dryness. Crystallization by partial evaporation of a solution in methanol results in the title compound: M.p. 271-272° C. (decomposition); FAB-MS: $(M+H)^+$=377; HPLC($Grad_{20-100}$) $t_{Ret}$=10.2.

The starting materials are prepared as follows:

4a) trans 1-(4-Isopropyl-cyclohexylamino)-4-[6-methoxy-(pyridin-3-yl)-methyl]-phthalazine Under $N_2$ atmosphere, in an ampoule 1.8 g (12.7 mMol) of trans 4-isopropyl-cyclohexylamine (preparation see *Arzneim. Forsch.* 1969, 19, 140) and 700 mg (2.4 mMol) of 1-chloro-4-[6-methoxy-pyridin-3-yl)methyl]phthalazine are heated during 14 h at 140° C. The suspension is dissolved by dilution with EtOAc, 1.5 ml of $NH_3$ solution (25%) and water, and the aqueous phase is removed and extracted twice with EtOAc. The organic phases are washed with water and brine, dried ($Na_2SO_4$) and evaporated. Crystallization from EtOAc/hexane 1:1 results in the title compound: M.p. 124-125° C.; FAB-MS: $(M+H)^+$=391; HPLC($Grad_{20-100}$) $t_{Ret}$12.4.

Example 5 trans 1-(2-Isopropyl-[1,3]dioxan-5-ylamino)-4-[6-hydroxy-(pyridin-3-yl)-methyl]-phthalazine Under $N_2$ atmosphere, 320 mg (2.2 mMol) of trans-2-isopropyl-[1,3]dioxan-5-ylamine and 400 mg (1.1 mMol) of 1-iodo-4-[6-hydroxy-pyridin-3-yl)methyl]phthalazine in 4 ml of tributylamine are heated for 8 h at 85° C. The reaction mixture is taken up by dilution with EtOAc and a small amount of methanol and diluted. $NaHCO_3$ solution, and the aqueous phase is removed and extracted twice with EtOAc. The organic phases are washed with water and brine, dried ($Na_2SO_4$) and evaporated to dryness. Reversed phase medium-pressure chromatography (water/acetonitrile/TFA) yields the title compound: $^1H$ NMR (DMSO-$d_6$) δ 11.4 (s, 1H), 8.28 und 8.12 (2d, 2 HC), 7.87 (m, 2 HC), 7.33 (m, 2 HC), 6.99 (s, HN), 6.24 (d, HC), 4.54 (m, 1H), 4.27 (m, 3H), 4.19 (s, $H_2C$), 3.59 (t, 2H), 1.79 (m, 1H), 0.92 (d, 2 $H_3C$); FAB-MS: $(M+H)^+$=381; HPLC($Grad_{20-100}$) $t_{Ret}$=7.9.

The starting materials are obtained as follows:

5a) 1-Iodo-4-[6-hydroxy-pyridin-3-yl)methyl]phthalazine

Excluding humidity, 0.5 ml (3.6 mMol) of Me₃SiI are added to 500 mg (1.7 mMol) of 1-chloro-4-[6-methoxy-pyridin-3-yl)methyl]phthalazine (Ex. 3e) in 20 ml chloroform and stirred at 60° C. After 5 h and 20 h of agitating, again each time 0.5 ml of Me₃SiI are added. After a total of 38 h, the mixture is cooled. Suction filtration and washing with chloroform results in the title compound which is used directly in Ex. 5: FAB-MS: (M+H)⁺=364; HPLC(Grad$_{20\text{-}100}$) t$_{Ret}$=8.3.

5b) 2-Benzyloxy-carbonylamino-1,3-propandiole

On an ice bath, 11.7 g (85 mMol) of K₂CO₃ and 10.5 ml (95%; 71 mMol) of benzyl chloroformate are added to a solution of 5.4 g (59 mMol) of 2-amino-1,3-propandiole in 50 ml of THF and 5 ml of water. After 1 h at 0° C., the mixture is stirred overnight at RT. The mixture is then diluted with EtOAc, the water is removed with solid Na₂SO₄, filtration follows and the residue is washed with EtOAc. During evaporation of the filtrate, the title compound is crystallizing out and is filtered off and washed with hexane: M.p. 108-109° C.; FAB-MS: (M+H)⁺=226.

5c) Benzyl-(2-isopropyl-[1,3]dioxan-5-yl)-carbamate

Under water separation, a solution of 10.1 g (44.8 mMol) of 2-benzyloxy-carbonylamino-1,3-propandiole, 123 mg of p-toluene-sulfonic acid and 4.2 ml (46 mMol) of isobutyraldehyde is boiled in 100 ml of benzene. After 5 h, again 4.2 ml of isobutyraldehyde are added. After 16 h the mixture is cooled down. This results in the precipitation of platelets. Filtration and washing with hexane produces trans-benzyl-(2-isopropyl-[1,3]dioxan-5-yl)-carbamate: M.p. 152° C.; FAB-MS: (M+H)⁺=226. Washing of the filtrate with NaHCO₃ solution, water and brine, drying (Na₂SO₄) and evaporation yields a cis-/trans mixture of the title compound from which, by crystallization from boiling toluene (with a small amount of p-toluenesulfonic acid) more of the trans isomer is obtained.

5e) trans 2-Isopropyl-[1,3]dioxan-5-ylamine

Hydrogenation of 4.07 g (14.6 mMol) of trans-benzyl-(2-isopropyl-[1,3]dioxan-5-yl)-carbamate in 80 ml of EtOAc in the presence of 0.4 g of 10% Pd/C, followed by filtration through Celite and evaporation, yields the title compound: ¹H NMR (CDCl₃) δ 4.11 (m, 3H), 3.20 (t, 10.5 Hz, 2H), 3.04 (m, 1H), 1.80 (m, 1H), 1.56 (sb, H₂N), 0.93 (d, 6H).

In analogy to Ex. 3, the following derivatives of structural type A are obtained from which by cleavage (Me₃SiI/hydrolysis) the respective compounds of structural type B are obtained:

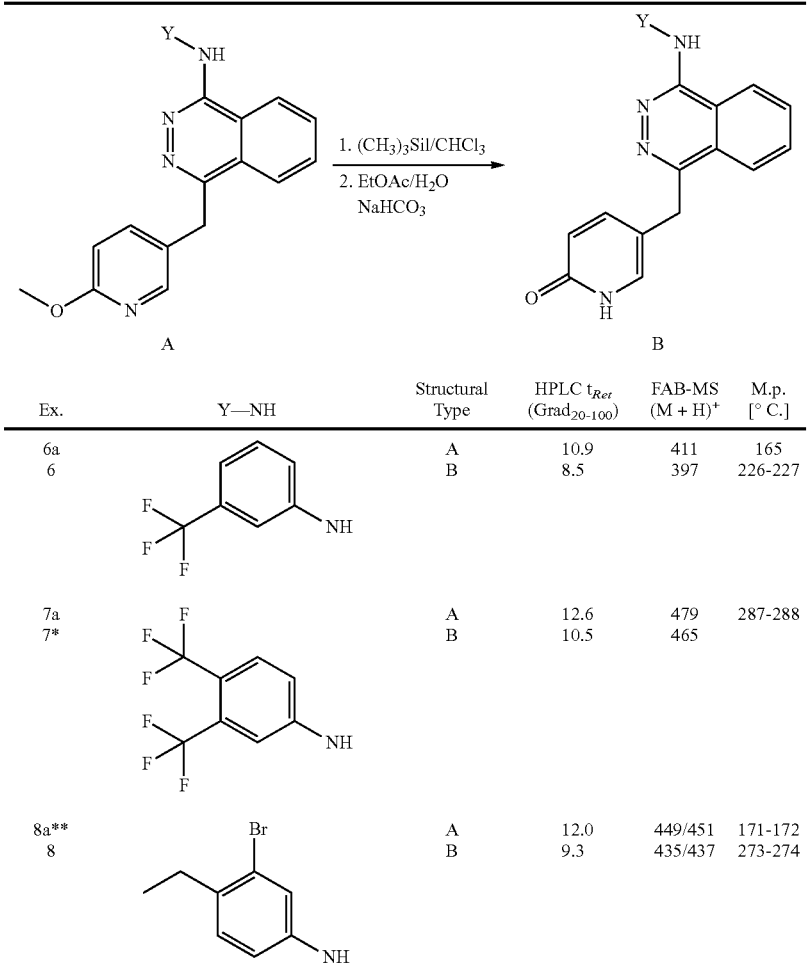

| Ex. | Y—NH | Structural Type | HPLC t$_{Ret}$ (Grad$_{20\text{-}100}$) | FAB-MS (M + H)⁺ | M.p. [° C.] |
|---|---|---|---|---|---|
| 6a | | A | 10.9 | 411 | 165 |
| 6 | | B | 8.5 | 397 | 226-227 |
| 7a | | A | 12.6 | 479 | 287-288 |
| 7* | | B | 10.5 | 465 | |
| 8a** | | A | 12.0 | 449/451 | 171-172 |
| 8 | | B | 9.3 | 435/437 | 273-274 |

-continued

| Ex. | Y—NH | Structural Type | HPLC $t_{Ret}$ (Grad$_{20\text{-}100}$) | FAB-MS (M + H)$^+$ | M.p. [° C.] |
|---|---|---|---|---|---|
| 9a | (3-trifluoromethyl-2-methylphenyl)NH | A |  | 425 | 183-184 |
| 9* |  | B |  | 411 |  |
| 10a*** | (3-bromo-4-tert-butylphenyl)NH | A | 12.6 | 477/479 | 168-169 |
| 10* |  | B | 10.4 | 463/465 | 277-278 |
| 11a | (3-trifluoromethyl-2-fluorophenyl)NH | A |  |  |  |
| 11 |  | B |  |  |  |
| 12a | (3-bromo-4-methylphenyl)NH | A |  |  |  |
| 12 |  | B |  |  |  |

*obtained directly as by-product of the reaction of chloro-4-[6-methoxy-pyridin-3-yl)methyl]phthalazine with the respective aniline derivative and separated off by column chromatography.
**preparation of 3-bromo-4-ethyl-aniline see Ex. 2a.
***analogously, 3-bromo-4-(tert-butyl)-aniline is obtained by hydrogenation of 3-bromo-4-(tert-butyl)-nitrobenzene (Maybridge).

Example 13 trans-1-(2-Isopropyl-[1,3]dioxan-5-ylamino)-4-[6-methoxy-(pyridin-3-yl)-methyl]phthalazin In analogy to Example 4a, starting from 408 mg (2.8 mMol) of trans-2-isopropyl[1,3]dioxan-5-ylamine (Ex. 5e) and 400 mg (1.4 mMol) 1-chloro-4-[6-methoxy-pyridin-3-yl)methyl]phthalazine, the title compound is obtained: m.p. 186-187° C.; FAB-MS: (M+H)$^+$=395; HPLC(Grad$_{20\text{-}100}$) $t_{Ret}$=9.7.

In analogy to Ex. 2, cleavage of derivatives of structural type A with Me$_3$Sil and hydrolysis yields the respective compounds of structural type B:

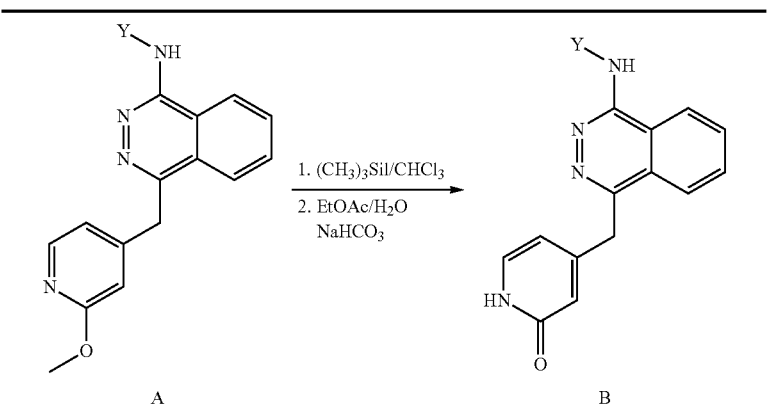

| Expl. | Y—NH | Struktural Type | HPLC $t_{Ret}$ (Grad$_{20-100}$) | FAB-MS (M + H)$^+$ | Smp. [° C.] | NVP— |
|---|---|---|---|---|---|---|
| 14a | Br-substituted methylphenyl-NH | A | 11.4 | 435/437 | 156-157 | ABH059 |
| 14 | | B | | | | |
| 15a | 3-chloro-5-trifluoromethylphenyl-NH | A | 12.5 | 445 | 151-152 | ABH442 |
| 15* | | B | | | | |
| 16a** | 4-isopropyl-3-methylphenyl-NH | A | 12.3 | 399 | 273 | ABH443 |
| 16 | | B | | | | |

Example 17

1-(4-tert-Butyl-anilino)-4-[5-bromo-6-methoxy-(pyridin-3-yl)-methyl]phthalazine (a) and 1-(4-tert-butyl-anilino)-4-[5-bromo-6-hydroxy-(pyridin-3-yl)-methyl]phthalazine (b)

Under N$_2$ atmosphere, 0.84 ml (5.33 mMol) of 4-tert-butyl-aniline and 1.8 ml 4 N HCl/dioxane are added to 1.80 g (72%; 3.55 mMol) of 1-chloro-4-[5-bromo-6-methoxy-(pyridin-3-yl)-methyl]phthalazine containing 1-chloro-4-[5-bromo-6-hydroxy-(pyridin-3-yl)-methyl]phthalazine in 30 ml of dioxane containing 17 vol % of isopropanol. After stirring for 25 min at 90° C., the yellow suspension is cooled to RT and filtered, washed with dioxane and dried in vacuo. Mother liquors are evaporated, diluted in 5 ml MeOH, EtOAc, and NaHCO$_3$ solution. The aqueous phase is removed and extracted twice with EtOAc. The organic layers are washed with water and brine, dried (Na$_2$SO$_4$) and concentrated in vacuo. Column chromatography of crystals and mother liquors (SiO$_2$; CH$_2$Cl$_2$/EtOAc 4:1 then CH$_2$Cl$_2$/MeOH 9:1) yields a followed by b. a: ES-MS: (M+H)$^+$=477/479; HPLC (Grad$_{20-100}$) $t_{Ret}$=14.1; b: ES-MS: (M+H)$^+$=463/465; HPLC (Grad$_{20}$-100) $t_{Ret}$=11.1.

The starting materials are prepared as follows:

17a) 5-Bromo-6-methoxy-pyridin-3-carbaldehyde (see *Eur. J. Med. Chem.-Chim. Ther.* 1977, 12, 531) 54.8 g (400 mMol) 6-methoxy-3-pyridinecarbaldehyde (Aldrich) are dissolved in 180 ml of acetic acid. 63.8 g (778 mMol) sodium acetate are added portionwise (slightly exothermic). Then a solution of 30 ml (582 mMol) of bromine in 120 ml of acetic acid is added dropwise during 30 min. The mixture is stirred for 5 h at 90° C., then cooled to RT and concentrated partially in vacuo. The residue is diluted with icewater, neutralized to pH 7.5 with 4 N NaOH and extracted with 4 portions of EtOAc. The organic layers are washed twice with water and brine, dried (Na$_2$SO$_4$) and concentrated in vacuo. Column chromatography (SiO$_2$; CH$_2$Cl$_2$) of the resulting oil and crystallization from CH$_2$Cl$_2$/hexane gives the title compound: mp: 94-95° C.

17b) 3-[1-(5-Bromo-6-methoxy-pyridin-3-yl)-methyliden]-3.H.-isobenzofuran-1-one

Under N$_2$ atmosphere, 8.0 g (37 mMol) 5-bromo-6-methoxy-pyridin-3-carbaldehyde are dissolved in 200 ml of THF. To the ice-cooled solution, 17.5 g (40.7 mMol) of 1,3-dihydro-3-oxo-1-iso-benzofuranyl-triphenyl-phosphonium chloride (preparation see *J. Organomet. Chem.* 1972, 42, 391) are added followed by 5.7 ml (40.8 mMol) of triethylamine. After 18 h at 0° C., the solid [OP(C$_6$H$_5$)$_3$] is filtered off, washed with THF and discarded. The filtrate is concentrated, redissolved in 1 l of EtOAC and washed with water and brine. The aqueous layers are extracted with EtOAc, the organic phases combined, dried (Na$_2$SO$_4$) and concentrated to the title compound [E/Z-mixture; containing OP(C$_6$H$_5$)$_3$]: FAB-MS: (M+H)$^+$=332/334; HPLC(Grad$_{20-100}$) t$_{Ret}$=15.5/16.7.

17c) 4-[5-Bromo-6-methoxy-(pyridin-3-yl)-methyl]phthalazin-1(2H)-one

A solution of 26.6 mMol of the above product in 180 ml of THF is heated to 70° C. under an atmosphere of nitrogen. Then 3.12 ml (80 mMol; 80% solution in H$_2$O) of hydrazine hydrate are added dropwise. After stirring for 90 min at 70° C., the reaction mixture is cooled to RT and partially concentrated in vacuo. The crystallized product is filtered off, washed with EtOAc and recrystallized from EtOAc yielding the title compound: mp: 227-228° C.; FAB-MS: (M+H)$^+$=346/348; HPLC(Grad$_{20-100}$) t$_{Ret}$=12.2.

17d) 1-Chloro-4-[5-bromo-6-methoxy-(pyridin-3-yl)-methyl]phthalazine

To a suspension of 1.38 g (4.00 mMol) of 4-[5-bromo-6-methoxy-(pyridin-3-yl)-methyl]phthalazin-1(2H)-one and 1.33 g (8.0 mMol) of Et$_4$NCl in 75 ml of acetonitrile under N$_2$-atmosphere, 1.01 ml (8.0 mMol) of N,N-dimethyl-aniline and 8.79 ml (96 mMol) of POCl$_3$ are added. After heating the mixture for 1 h to 90° C., the resulting solution is cooled to RT, pored into 400 ml of icewater and 500 ml sat. NaHCO$_3$ solution and extracted with 3 portions of EtOAc. The organic phases are washed twice with water and brine, dried (Na$_2$SO$_4$) and concentrated to the title compound containing some 1-chloro-4-[5-bromo-6-hydroxy-(pyridin-3-yl)-methyl]phthalazine: FAB-MS: (M+H)$^+$=364/366; HPLC(Grad$_{20-100}$) t$_{Ret}$=14.5.

Example 18

1-(4-tert-Butyl-anilino)-4-[5-(furan-2-yl)-6-hydroxy-(pyridin-3-yl)-methyl]phthalazine In analogy to Ex. 3, treatment of a solution of 1-(4-tert-butyl-anilino)-4-[5-(furan-2-yl)-6-methoxy-(pyridin-3-yl)-methyl]phthalazine in CHCl$_3$ with Me$_3$Sil, followed by hydrolysis gives the title compound. ES-MS: (M+H)$^+$=451; HPLC(Grad$_{20-100}$) t$_{Ret}$=12.6.

The starting material is prepared as follows:

18a) 1-(4-tert-Butyl-anilino)-4-[5-(furan-2-yl)-6-methoxy-(pyridin-3-yl)-methyl]phthalazine To a solution of 366 mg (0.76 mMol) 1-(4-tert-butyl-anilino)-4-[5-bromo-6-methoxy-(pyridin-3-yl)-methyl]phthalazine (Ex. 17: a) in 7 ml degassed DMF under a N$_2$-atmosphere are added 174 mg (0.15 mMol) of Pd[P(C$_6$H$_5$)$_3$]$_4$ and 0.6 ml (1.9 mMol) of 2-tributylstannyl-furan (Aldrich). After 4 h stirring at 100° C., the reaction mixture is diluted with EtOAc and washed with NaHCO$_3$ solution. The aqueous layers are extracted twice with EtOAc, the organic phases washed with water, brine, dried (Na$_2$SO$_4$) and concentrated in vacuo. Column chromatography (SiO$_2$; CH$_2$Cl$_2$/Et$_2$O 7:3) and crystallization from DIPE yields the title compound. mp: 180-182° C.; ES-MS: (M+H)$^+$=465; HPLC(Grad$_{20-100}$) t$_{Ret}$=15.0.

Example 19

1-(4-tert-Butyl-anilino)-4-[5-(thiazol-2-yl)-6-hydroxy-(pyridin-3-yl)-methyl]phthalazine Can be obtained analogously to Ex. 18 from 1-(4-tert-butyl-anilino)-4-[5-(thiazol-2-yl)-6-methoxy-(pyridin-3-yl)-methyl]phthalazine by deprotection with Me$_3$Sil. ES-MS: (M+H)$^+$=468; HPLC(Grad$_{20-100}$) t$_{Ret}$=11.9.

The starting material is prepared as follows:

19a) 1-(4-tert-Butyl-anilino)-4-[5-(thiazol-2-yl)-6-methoxy-(pyridin-3-yl)-methyl]phthalazine Can be obtained analogously to Ex. 18a from 1-(4-tert-butyl-anilino)-4-[5-bromo-6-methoxy-(pyridin-3-yl)-methyl]phthalazine and 2-tributylstannyl-thiazol (supplier: Frontier Scientific; Logan/USA). MS: (M+H)$^+$=482; HPLC (Grad$_{20-100}$) t$_{Ret}$=14.6.

Example 20

1-(4-tert-Butyl-anilino)-4-[5-ethylamino-6-hydroxy-(pyridin-3-yl)-methyl]phthalazine In analogy to Ex. 3, treatment of a solution of 1-(4-tert-butyl-anilino)-4-[5-ethylamino-6-methoxy-(pyridin-3-yl)-methyl]phthalazine in CHCl$_3$ with Me$_3$Sil, followed by hydrolysis gives the title compound. ES-MS: (M+H)$^+$=428; HPLC(Grad$_{20-100}$) t$_{Ret}$=11.9.

The starting material is prepared as follows:

20a) 1-(4-tert-Butyl-anilino)-4-[5-ethylamino-6-methoxy-(pyridin-3-yl)-methyl]phthalazine A mixture of 400 mg (0.84 mMol) 1-(4-tert-butyl-anilino)-4-[5-bromo-6-methoxy-(pyridin-3-yl)-methyl]phthalazine (Ex. 17: a), 52 mg R(+)-BINAP [R(+)-2,2'-bis-(diphenylphosphino)-1,1'-binaphthalin]; 0.08 mMol], 22 mg Pd$_2$(dba)$_3$CHCl$_3$ [tris(dibenzylideneacetone)dipalladium (0) chloroform complex; 0.02 mMol] and 161 mg (1.68 mMol) of sodium-tert-butylate is prepared in 10 ml degassed DMF in a sealed tube under a N$_2$-atmosphere. Then 2.5 ml (5 mMol) of a 2 N solution of ethylamine in THF are added. After 58 h stirring at 70° C., the reaction mixture is diluted with EtOAc and sat. NaHCO$_3$ solution. The aqueous layers are extracted twice with EtOAc, the organic phases washed with sat. NaHCO$_3$ solution, brine, dried (Na$_2$SO$_4$) and concentrated in vacuo. Column chromatography (SiO$_2$; CH$_2$Cl$_2$/Aceton 5:1)

yields the title compound, containing 1-(4-tert-butyl-anilino)-4-[6-methoxy-(pyridin-3-yl)-methyl]phthalazine. The title compound is then isolated by preparative MPLC. ES-MS: (M+H)$^+$=442; HPLC(Grad$_{20-100}$) $t_{Ret}$=13.2.

In analogy to the above described examples, the following derivatives can be obtained:

| Expl. | R | R' | Struktural Type |
|---|---|---|---|
| | | | A |
| | | | B |
| 21a | pyridin-2-yl | H | A |
| 21 | pyridin-2-yl | H | B |
| 22a | pyridin-2-yl | Cl | A |
| 22 | pyridin-2-yl | Cl | B |
| 23a | thien-3-yl | H | A |
| 23 | thien-3-yl | H | B |
| 24a | thien-3-yl | n-propyl | A |
| 24 | thien-3-yl | n-propyl | B |
| 25a | 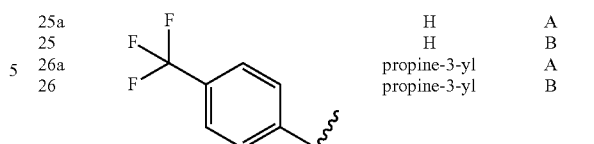 | H | A |
| 25 | | H | B |
| 26a | | propine-3-yl | A |
| 26 | | propine-3-yl | B |
| 27a | 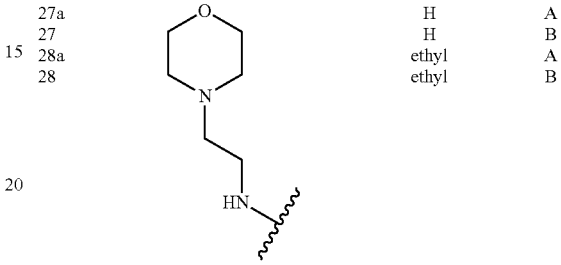 | H | A |
| 27 | | H | B |
| 28a | | ethyl | A |
| 28 | | ethyl | B |

Example 29

1-(4-Fluoro-2-methyl-1H-indol-5-yloxy)-4-[6-hydroxy-(pyridin-3-yl)-methyl]phthalazine In analogy to Ex. 3, treatment of a solution of 1-(4-fluoro-2-methyl-1H-indol-5-yloxy)-4-[6-methoxy-(pyridin-3-yl)-methyl]phthalazine in CHCl$_3$ with Me$_3$SiI, followed by hydrolysis gives the title compound.

The starting material is prepared as follows:

29a) 1-(4-Fluoro-2-methyl-1H-indol-5-yloxy)-4-[6-methoxy-(pyridin-3-yl)-methyl]phthalazine Heating of a mixture of 1-chloro-4-[6-methoxy-(pyridin-3-yl)-methyl]phthalazine (Ex. 3e), 4-fluoro-5-hydroxy-2-methyl-1H-indole (preparation see WO 00/47212; Ex. 237) and K$_2$CO$_3$ in DMF yields the title compound.

Example 30

Cyp$_{450}$-Inhibition

By the help of recombinant CyP 450 enzymes, the corresponding IC$_{50}$ values for the compounds of formula I are determined. This allows to demonstrate that the compounds of formula I, when compared with compounds form the prior art, e.g. as described in WO 00/59509, have advantageous properties. Description of the Assay: Fluorescence-labelled substrate compounds are incubated with different concentrations of test compound of formula I with recombinant Cytochrome P$_{450}$ isoenzymes. From these data, the concentration is determined at which 50% of the activity of the enzyme is inhibited when compared to the activity in the absence of inhibitor (→IC$_{50}$). For details see above in the general description.

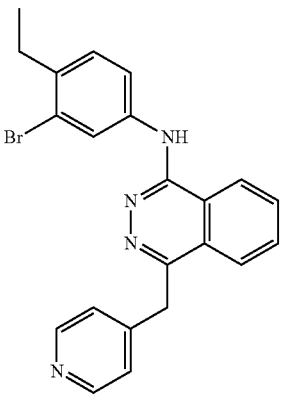

| Inhibition of Cytochrome-IC$_{50}$ [μM] | WO 00/59509 (Ex. 14q) | Ex. 8 of the present disclosure |
| --- | --- | --- |
| Cyp3A4 | <1 | 2.8 |
| Cyp2C8 | 5 | >10 |
| Cyp2C9 | <1 | 3.5 |

This shows that there is an at least more than two-fold lower inhibition of the three mentioned cytochromes for Example 8 of the present disclosure when compared with Ex. 14 q from WO 00/59509, and that the IC50 is larger than 1 μM.

Example 31

Test for Activity against Flt-1 VEGF-Receptor Tyrosine Kinase

The test is conducted using Flt-1 VEGF-receptor tyrosine kinase, as described hereinabove. The IC$_{50}$ values determined are given below, insofar as they have been accurately determined:

| Title compound from Example | IC$_{50}$ (μmol) |
| --- | --- |
| Example 1 d) | 1.2 |
| Example 2 d) | 1.9 |

Example 32

Soft Capsules 5000 soft gelatin capsules, each comprising as active ingredient 0.05 g of one of the compounds of formula I mentioned in the preceding Examples, are prepared as follows:

| Composition | |
| --- | --- |
| Active ingredient | 250 g |
| Lauroglykol | 2 litre |

Preparation Process: The pulverized active ingredient is suspended in Lauroglykol® (propylene glycol laurate, Gattefossé S. A., Saint Priest, France) and ground in a wet pulverizer to produce a particle size of about 1 to 3 μm. Then 0.419 g portions of the mixture are introduced into soft gelatin capsules using a capsule-filling machine.

The invention claimed is:

1. A compound of the formula I,

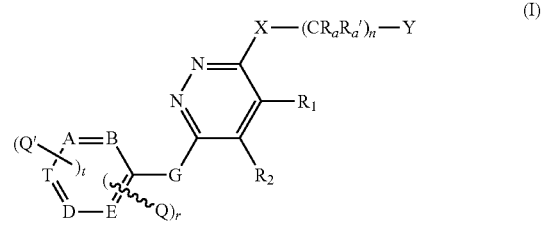

wherein
r is 1 or 2, n is 0-3,
t is 0, 1 or 2,
R1 and R2
together form a bridge of subformula 1**,

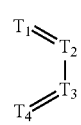

wherein one or two of the ring members $T_1$, $T_2$, $T_3$ and $T_4$ are nitrogen, and the others are in each case CH, and the bond is achieved via atoms $T_1$ and $T_4$;
G is CH$_2$;
A is N and B, D, E and T are CH;
Q is either lower alkoxy or O, with the proviso that if Q is lower alkoxy, the waved line representing the bonding of Q is a single bond and the ring carrying Q has three double bonds, and if Q is O, the waved line representing the bonding of Q is a double bond and for each Q=O, one of the double bonds in the ring is changed to a single bond; and with the proviso that any Q is bonded to a ring C atom;

Q' is halogen, $NHR^Q$, $NR^Q_2$, $OR^Q$, $SR^Q$, alkyl, aryl-alkyl, cycloalkyl-alkyl, perfluoroalkyl, acyl, substituted or unsubstituted aryl, or substituted or unsubstituted hetaryl, wherein $R^Q$ represents acyl, alkyl, or alkyl substituted by hydroxy, halogen, substituted or unsubstituted aryl, substituted or unsubstituted cycloalkyl or substituted or unsubstituted heterocyclyl;

$R_a$ and $R_a'$ are each independently H, halogen or lower alkyl;

X is imino, oxa, or thia; and

Y is hydrogen, substituted or unsubstituted aryl, substituted or unsubstituted heteroaryl, or unsubstituted or substituted cycloalkyl;

or an N-oxide of a compound of formula I, wherein 1 or more N atoms carry an oxygen atom;

or a tautomer or mixture of tautomers of a compound of formula I or an N-oxide thereof;

or a pharmaceutically acceptable salt of a compound of formula I, of an N-oxide or of a tautomer or mixture of tautomers thereof.

2. A compound of the formula I according to claim 1, wherein r is 1 or 2, n is 0 to 3, t is 0, $R_1$ and $R_2$ together form a bridge of subformula 1**, wherein one or two of the ring members $T_1$, $T_2$, $T_3$ and $T_4$ are nitrogen, and the others are in each case CH, and the bond is achieved via atoms $T_1$ and $T_4$;

G is $CH_2$;

A is N and B, D, E and T are CH;

Q is either lower alkoxy or O, with the proviso that if Q is lower alkoxy, the waved line representing the bonding of Q is a single bond and the ring carrying Q has three double bonds, and if Q is O, the waved line representing the bonding of Q is a double bond and for each Q=O, one of the double bonds in the ring is changed to a single bond; and with the proviso that any Q is bonded to a ring C atom;

$R_a$ and $R_a'$ are each independently H, halogen or lower alkyl;

X is imino, oxa, or thia; and

Y is hydrogen, aryl, heteroaryl, or unsubstituted or substituted cycloalkyl;

or an N-oxide of a compound of formula I, wherein 1 or more N atoms carry an oxygen atom;

or a tautomer or mixture of tautomers of a compound of formula I or an N-oxide thereof;

or a pharmaceutically acceptable salt of a compound of formula I, of an N-oxide or of a tautomer or mixture of tautomers thereof.

3. A compound of formula I according to claim 1, wherein Q is O, with the proviso that the waved line representing the bonding of Q is a double bond and for each Q=O, one of the double bonds in the ring is changed to a single bond; and with the proviso that any Q is bonded to a ring C atom; and the other symbols have the meaning described in claim 1; an N-oxide of said compound of formula I, wherein 1 or more N atoms carry an oxygen atom; or a tautomer or mixture of tautomers of said compound of formula I or an N-oxide thereof; or a pharmaceutically acceptable salt of said compound of formula I, of an N-oxide or of a tautomer or mixture of tautomers thereof.

4. A compound of formula I according to claim 1 wherein r is 1 and A is NH, each of B, D and E is CH and T is C and Q is O bonded at T via a double bond;

tautomer or mixture of tautomers of said compound of formula I; or a pharmaceutically acceptable salt of said compound of formula I, or of a tautomer or mixture of tautomers thereof.

5. A pharmaceutical preparation comprising a compound of the formula I, an N-oxide thereof, a tautomer or mixture of tautomers of said compound of formula I or an N-oxide thereof; or a pharmaceutically acceptable salt of said compound of formula I, of an N-oxide or of a tautomer or mixture of tautomers thereof according to claim 1 and a pharmaceutically acceptable carrier.

6. A method for treating a warm-blooded animal in which an effective dose of a compound of formula I, an N-oxide thereof, a tautomer or mixture of tautomers of said compound of formula I or an N-oxide thereof; or a pharmaceutically acceptable salt of said compound of formula I, of an N-oxide or of a tautomer or mixture of tautomers thereof according to claim 1 is administered to a warm-blooded animal suffering from inflammatory rheumatic or rheumatoid diseases, or pain.

* * * * *